(12) United States Patent
Lebofsky et al.

(10) Patent No.: US 11,479,816 B2
(45) Date of Patent: Oct. 25, 2022

(54) NUCLEOTIDE SEQUENCE GENERATION BY BARCODE BEAD-COLOCALIZATION IN PARTITIONS

(71) Applicant: Bio-Rad Laboratories, Inc., Hercules, CA (US)

(72) Inventors: Ronald Lebofsky, Kensington, CA (US); Andrew Kohlway, Pleasanton, CA (US); Jennifer Chew, Sunnyvale, CA (US); Zachary Burkett, Walnut Creek, CA (US); Man Cheng, Danville, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 473 days.

(21) Appl. No.: 16/545,611

(22) Filed: Aug. 20, 2019

(65) Prior Publication Data
US 2020/0056231 A1   Feb. 20, 2020

Related U.S. Application Data

(60) Provisional application No. 62/720,014, filed on Aug. 20, 2018.

(51) Int. Cl.
| | | |
|---|---|---|
| *C12Q 1/6869* | (2018.01) | |
| *G16B 40/10* | (2019.01) | |
| *G16B 30/10* | (2019.01) | |

(52) U.S. Cl.
CPC .......... *C12Q 1/6869* (2013.01); *G16B 30/10* (2019.02); *G16B 40/10* (2019.02); *C12Q 2563/155* (2013.01); *C12Q 2563/185* (2013.01)

(58) Field of Classification Search
CPC ....... C12Q 1/6869; G16B 30/10; G16B 40/10
See application file for complete search history.

(56) References Cited

U.S. PATENT DOCUMENTS

| | | | |
|---|---|---|---|
| 2014/0378322 A1* | 12/2014 | Hindson | C12Q 1/6806 506/4 |
| 2015/0011432 A1 | 1/2015 | Saxonov | |
| 2017/0044525 A1 | 2/2017 | Kaper et al. | |
| 2017/0232417 A1* | 8/2017 | Lebofsky | C12Q 1/6806 506/16 |
| 2018/0016634 A1 | 1/2018 | Hindson et al. | |

FOREIGN PATENT DOCUMENTS

| | | |
|---|---|---|
| WO | 2015/200541 A1 | 12/2015 |
| WO | 2016/130868 A2 | 8/2016 |
| WO | 2017/120531 A1 | 7/2017 |

OTHER PUBLICATIONS

International Search Report and Written Opinion from PCT Application PCT/US2019/047239 dated Nov. 21, 2019; 15 pages.
Extended European Search Report in EP Appln. 19851177.6 dated May 6, 2022; 6 pages.
Lareau, C.A. et al.; "Droplet-based combinatorial indexing for massive-scale single-cell chromatin accessibility"; *Nature Biotechnology*; Nature Publishing Group US, New York; vol. 37, No. 8; Jun. 24, 2019; pp. 916-924.

* cited by examiner

*Primary Examiner* — Narayan K Bhat
(74) *Attorney, Agent, or Firm* — Kilpatrick Townsend and Stockton LLP

(57) ABSTRACT

Comparison of common sequencing reads from sequencing based on partition-based barcoding can be used to improve sequencing results. Increased loading of barcodes per partition can also improve sequencing results.

19 Claims, 18 Drawing Sheets

Specification includes a Sequence Listing.

SEQUENCE LISTING

```
<160> NUMBER OF SEQ ID NOS: 9

<210> SEQ ID NO 1
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tcgtcggcag cgtc                                                        14

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gtctcgtggg ctcgg                                                       15

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
agatgtgtat aagagacag                                                   19

<210> SEQ ID NO 4
<211> LENGTH: 33
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 4
tcgtcggcag cgtcagatgt gtataagaga cag                                    33

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gtctcgtggg ctcggagatg tgtataagag acag                                   34

<210> SEQ ID NO 6
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tttttttttt tt                                                           12

<210> SEQ ID NO 7
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
aaaaaaaaaa a                                                            11

<210> SEQ ID NO 8
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tttttttttt t                                                            11

<210> SEQ ID NO 9
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tttttttttt                                                              10
```

NUCLEOTIDE SEQUENCE GENERATION BY BARCODE BEAD-COLOCALIZATION IN PARTITIONS

CROSS-REFERENCES TO RELATED APPLICATIONS

The present application claims the benefit of U.S. Provisional Appln. No. 62/720,014 filed Aug. 20, 2018, the full disclosure which is incorporated herein by reference in its entirety for all purposes.

SEQUENCE LISTING

The instant application contains a Sequence Listing which has been submitted electronically in ASCII format and is hereby incorporated by reference in its entirety. Said ASCII copy, created on Feb. 28, 2022, is named 094868-1146674-116410US SL.txt and is 2,433 bytes in size.

BACKGROUND OF THE INVENTION

Beads conjugated to oligonucleotides are used in sequencing sample prep applications such as high-throughput single cell analysis having many different partitions (e.g., droplets). In order to uniquely identify each partition, the beads can be labeled with unique barcode sequences. However, in order to ensure that partitions have only one bead and thus are uniquely labeled by the barcode, bead concentrations are typically adjusted so that only about 1 out of 10 partitions are occupied by a bead. This results in low utilization of the partitions, sample loss and increases the amount of sample and reagents that are needed for detection of samples. Increasing bead concentrations would result in higher partition occupancy and greater utilization of partitions. The utilization of partitions would increase, sample loss would decrease and the amount of sample and reagents that are needed for detection of samples would be decreased. Conversely, higher bead concentrations would lead to a greater number of partitions having more than one bead. Thus, some partitioned samples would be labeled by more than one barcode. In some of these instances, the sample in a partition would be split between the more than one barcode resulting in an expected loss of sensitivity per barcode and for example overrepresentation of certain data points by virtue of having more than one data point generated from a single partition.

BRIEF SUMMARY OF THE INVENTION

In some embodiments, a method of generating a nucleotide sequence of a DNA template is provided. In some embodiments, the method comprises:
(a) partitioning a sample into a plurality of partitions comprising a particle comprising a solid support surface, the solid support surface having a plurality of oligonucleotide primers conjugated thereon, wherein the oligonucleotide primers comprise a barcode sequence and wherein different particles are distinguished by having different barcodes from one another (e.g., wherein at least a majority of the plurality of oligonucleotide primers conjugated to a solid support surface comprise the same barcode sequence), wherein at least some partitions have more than one particles per partition, and wherein different particles are conjugated to primers having different barcode sequences;
(b) providing in the partitions DNA template fragments to be sequenced; and
(c) in the partitions, linking oligonucleotide primers from the solid support to at least a fragment of DNA template, thereby forming barcoded DNA template fragments;
(d) combining barcoded DNA template fragments from multiple partitions;
(d) generating a plurality of sequencing reads of the barcoded DNA templates;
(e) determining in a pairwise manner percent of sequencing reads of DNA template fragments shared between different barcodes;
(f) comparing the determined percent of DNA template fragments shared between different barcodes to a threshold value, wherein if two barcodes have a determined percent of identical DNA template fragments in common above the threshold value, the two barcodes are determined to be in the same partition; and
(g) generating a nucleotide sequence for the DNA template from the plurality of sequencing reads, wherein generating the nucleotide sequence comprises treating sequencing reads having different barcodes determined to be in the same partition as being from the same partition;
thereby generating a nucleotide sequence of a DNA template.

In some embodiments, the DNA template fragments comprise heterologous end adaptor sequences.

In some embodiments, the providing comprises randomly cleaving template DNA. In some embodiments, the randomly cleaving comprises contacting the template DNA with a transposase that introduces heterologous end adaptor sequences into the template DNA to form template DNA fragments comprising the heterologous end adaptor sequences. In some embodiments, the randomly cleaving comprises contacting the transposase to DNA in nuclei of cells. In some embodiments, the transposase links pairs of template DNA fragments thereby preserving contiguity of the template DNA in the partitions.

In some embodiments, the partitioning results in an average or median of 1.0-5 particles per partition.

In some embodiments, at least 10%, 20%, 30%, 40%, 50%, 60% or 70% of the partitions have more than one particle per partition.

In any of the above embodiments, generating the nucleotide sequence can comprise excluding sequencing reads from partitions comprising more particles than would be predicted by a Poisson distribution.

In any of the above embodiments, generating the nucleotide sequence can comprise excluding sequencing reads from partitions comprising more particles than are physically possible as determined by the size of the particle in comparison to the size of the partition (e.g., droplet.

In some embodiments, the method comprises:
(a) partitioning a sample into a plurality of partitions comprising a particle comprising a solid support surface, the solid support surface having a plurality of oligonucleotide primers conjugated thereon, wherein the oligonucleotide primers comprise a barcode sequence and wherein different particles are distinguished by having different barcodes from one another (e.g., wherein at least a majority of the plurality of oligonucleotide primers conjugated to a solid support surface comprise the same barcode sequence), wherein at least 10%, 20%, 30%, 40%, 50%, 60% or 70% of the partitions have more than one particle per partition, and wherein different particles are conjugated to primers having different barcode sequences;
(b) providing in the partitions DNA template fragments to be sequenced; and (c) in the partitions, linking oligonucleotide primers from the solid support to at least a fragment of DNA template, thereby forming barcoded DNA template fragments;
(d) combining barcoded DNA template fragments from multiple partitions;
(d) generating a plurality of sequencing reads of the barcoded DNA templates;
(e) deconvoluting sequencing reads having different barcodes to the same partition when the sequencing reads were generated from the same partition; and
(f) generating a nucleotide sequence for the DNA template from the plurality of sequencing reads, wherein generating the nucleotide sequence comprises treating sequencing reads having different barcodes determined to be in the same partition as being from the same partition;
thereby generating a nucleotide sequence of a DNA template.

In some embodiments, the deconvoluting comprises comparing in a pairwise manner the determined percent of DNA template fragments shared between different barcodes to a threshold value, wherein if two barcodes have a determined percent of DNA template fragments in common above the threshold value, the two barcodes are determined to be in the same partition.

In some embodiments, the DNA template fragments comprise heterologous end adaptor sequences.

In some embodiments, the providing comprises randomly cleaving template DNA. In some embodiments, the randomly cleaving comprises contacting the template DNA with a transposase that introduces heterologous end adaptor sequences into the template DNA to form template DNA fragments comprising the heterologous end adaptor sequences. In some embodiments, the randomly cleaving comprises contacting the transposase to DNA in nuclei of cells. In some embodiments, the transposase links pairs of template DNA fragments thereby preserving contiguity of the template DNA in the partitions.

In some embodiments, the partitioning results in an average or median of 1.0-5 particles per partition.

In some embodiments, at least 10%, 20%, 30%, 40%, 50%, 60% or 70% of the partitions have more than one particle per partition.

In some embodiments, generating the nucleotide sequence comprises excluding sequencing reads from partitions comprising more particles than would be predicted by a Poisson distribution.

In some embodiments, the method comprises excluding sequencing reads from partitions comprising more particles than are physically possible as determined by the size of the particle in comparison to the size of the partition (e.g., droplet) droplet.

Also provided is a method of distinguishing differently barcoded sequence reads originating from different partitions from sequence reads having different barcodes but originating from the same partition. In some embodiments, the method comprises:
(a) partitioning a sample into a plurality of partitions comprising a particle comprising a plurality of oligonucleotide primers, wherein the oligonucleotide primers comprise a barcode sequence and wherein different particles are distinguished by having different barcodes from one another, wherein at least some partitions have more than one particles per partition, and wherein different particles are conjugated to primers having different barcode sequences;
(b) providing in the partitions DNA fragments;
(c) in the partitions, linking oligonucleotide primers from the particle to DNA fragments, thereby forming barcoded DNA fragments;
(d) combining barcoded DNA fragments from multiple partitions;
(d) generating a plurality of sequencing reads of the barcoded DNA;
(e) determining in a pairwise manner percent of sequencing reads of DNA fragments shared between different barcodes; and (f) comparing the determined percent of DNA fragments shared between different barcodes to a threshold value, wherein if two barcodes have a determined percent of identical DNA template fragments in common above the threshold value, the two barcodes are determined to be in the same partition.

In some embodiments, at least a majority of the plurality of oligonucleotide primers associated with a particle comprise the same barcode sequence.

In some embodiments, the DNA fragments are sample DNA. In some embodiments, methyl cytosines in the sample DNA has been converted for methylation analysis prior to the partitioning. In some embodiments, the sample DNA has been bisulfite-treated prior to the partitioning.

In some embodiments, the partitions comprise sample cells and the sample DNA is from the sample cells. In some embodiments, the partitions comprise sample cells and the sample DNA is cDNA generated from the sample cells.

In some embodiments, the method further comprises pre-encapsulating the sample cells in partitions.

In some embodiments, the partitions further contain sample DNA to be sequenced and the DNA fragments are exogenous to the sample DNA.

In some embodiments, the method further comprises generating a nucleotide sequence for the sample DNA, wherein generating the nucleotide sequence comprises treating sequencing reads having different barcodes determined to be in the same partition as being from the same partition, thereby generating a nucleotide sequence of a DNA template.

In some embodiments, the DNA fragments comprise heterologous end adaptor sequences.

In some embodiments, the providing comprises randomly cleaving DNA. In some embodiments, the randomly cleaving comprises contacting the DNA with a transposase that introduces heterologous end adaptor sequences into the DNA to form DNA fragments comprising the heterologous end adaptor sequences. In some embodiments, the randomly cleaving comprises contacting the transposase to DNA in nuclei of cells. In some embodiments, the transposase links pairs of DNA fragments thereby preserving contiguity of the template DNA in the partitions.

In some embodiments, the partitioning results in an average or median of 0.1-5 or 1.0-5 particles per partition. In some embodiments, at least 10%, 20%, 30%, 40%, 50%, 60% or 70% of the partitions have more than one particle per partition.

In some embodiments, generating the nucleotide sequence comprises excluding sequencing reads from partitions comprising more particles than would be predicted by a Poisson distribution.

In some embodiments, the method comprises excluding sequencing reads from partitions comprising more particles than are physically possible as determined by the size of the particle in comparison to the size of the partition.

In some embodiments, the particle is composed of a hydrogel that contains the oligonucleotides. In some embodiments, the particle comprises a solid surface to which the oligonucleotides are conjugated. In some embodiments, the oligonucleotides are released from the particles in the partitions.

BRIEF DESCRIPTION OF THE DRAWINGS

FIG. 8 discloses SEQ ID NOS 6, 6, 7 and 7, respectively, in order of appearance.

FIG. 9 discloses SEQ ID NOS 7, 7, 7, 7, 8, 9, 7, 8, 8 and 8, respectively, in order of appearance.

FIG. 10 discloses SEQ ID NOS 9, 7, 8, 8, 8 and 8, respectively, in order of appearance.

FIG. 11 discloses SEQ ID NOS 7, 7, 9 and 9, respectively, in order of appearance.

DEFINITIONS

Figure 1:
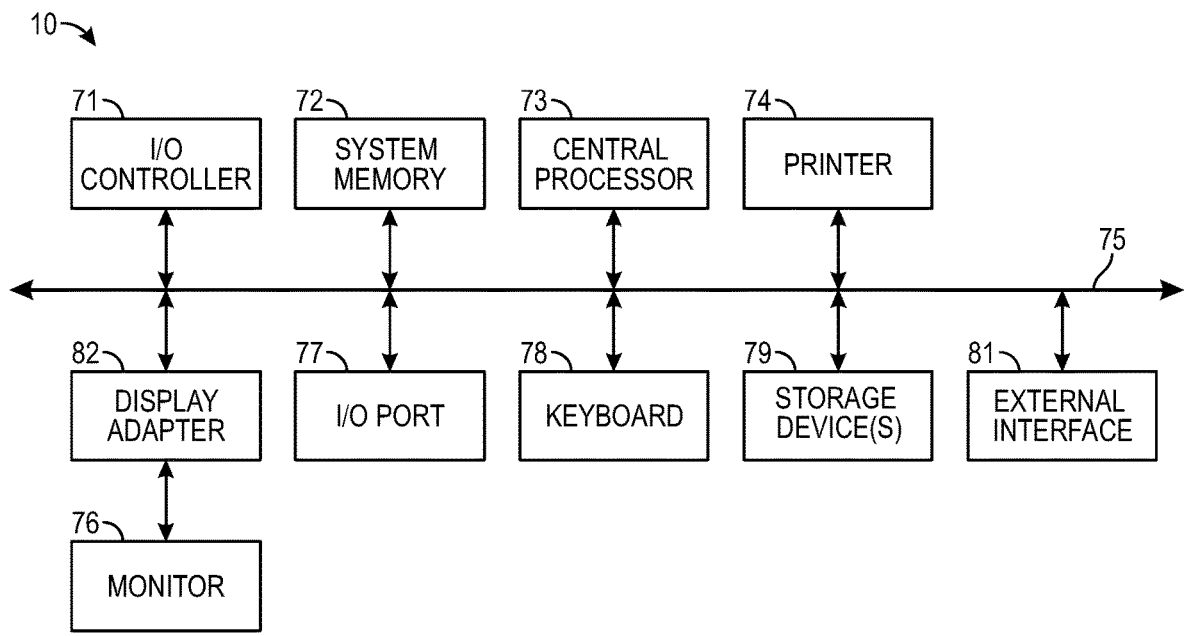
FIG. 1 illustrates a computer system.
Figure 2:
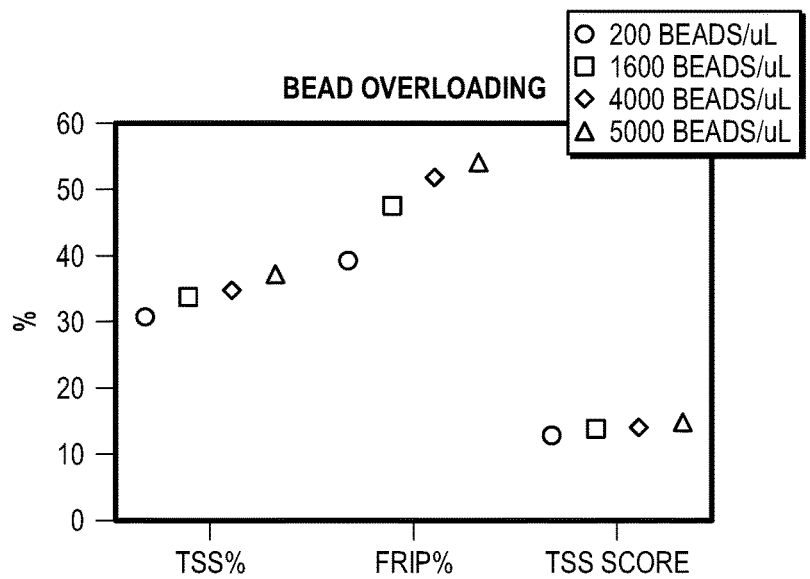
FIG. 2 illustrates improved sequencing data when increasing numbers of barcoded beads are used per partition.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, analytical chemistry, and nucleic acid chemistry and hybridization described below are those well-known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document.

"Random" includes absolutely random and quasi-random events. For example, "randomly cleaving" DNA includes cleaving DNA with a TN5 transposase that cleaves DNA in a quasi-random fashion, for example, sufficiently random such that when the cut DNA is distributed among different partitions, each partition has a unique set of fragments.

"Heterologous end adaptor sequences" refer to heterologous sequences, usually added in the form of an oligonucleotide, that provide a common sequence at the ends of template DNA. Such adaptor sequences allow for ease of manipulation of different template DNA fragments.

The term "amplification reaction" refers to any in vitro method for multiplying the copies of a target sequence of nucleic acid in a linear or exponential manner. Such methods include, but are not limited to, polymerase chain reaction (PCR); DNA ligase chain reaction (LCR); QBeta RNA replicase and RNA transcription-based amplification reactions (e.g., amplification that involves T7, T3, or SP6 primed RNA polymerization), such as the transcription amplification system (TAS), nucleic acid sequence based amplification (NASBA), and self-sustained sequence replication (3SR); single-primer isothermal amplification (SPIA), loop mediated isothermal amplification (LAMP), strand displacement amplification (SDA); multiple displacement amplification (MDA); rolling circle amplification (RCA); as well as others known to those of skill in the art. See, e.g., Fakruddin et al., *J. Pharm Bioallied Sci.* 2013 5(4):245-252.

"Amplifying" refers to a step of submitting a solution to conditions sufficient to allow for amplification of a polynucleotide if all of the components of the reaction are intact. Components of an amplification reaction include, e.g., primers, a polynucleotide template, polymerase, nucleotides, and the like. The term "amplifying" typically refers to an "exponential" increase in target nucleic acid. However, "amplifying" as used herein can also refer to linear increases in the numbers of a select target sequence of nucleic acid, such as is obtained with cycle sequencing or linear amplification.

"Polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and PCR Protocols: A Guide to Methods and Applications, Innis et al., eds, 1990. Exemplary PCR reaction conditions typically comprise either two or three step cycles. Two step cycles have a denaturation step followed by a hybridization/elongation step. Three step cycles comprise a denaturation step followed by a hybridization step followed by a separate elongation step.

A "primer" refers to a polynucleotide sequence that hybridizes to a sequence on a target nucleic acid and optionally serves as a point of initiation of nucleic acid synthesis. Primers can be of a variety of lengths. In some embodiments, a primer is less than 100 or 50 nucleotides in length, e.g., from about 10 to about 900, from about 15 to about 80, or from about 30-85 to about 30 nucleotides in length. The length and sequences of primers for use in an amplification reaction (e.g., PCR) can be designed based on principles known to those of skill in the art; see, e.g., PCR Protocols: A Guide to Methods and Applications, Innis et al., eds, 1990. The primer can include or be completely formed from DNA, RNA or non-natural nucleotides. In some embodiments, a primer comprises one or more modified and/or non-natural nucleotide bases. In some embodiments, a primer comprises a label (e.g., a detectable label).

A nucleic acid, or portion thereof, "hybridizes" to another nucleic acid under conditions such that non-specific hybridization is minimal at a defined temperature in a physiological buffer. In some cases, a nucleic acid, or portion thereof, hybridizes to a conserved sequence shared among a group of target nucleic acids. In some cases, a primer, or portion thereof, can hybridize to a primer binding site if there are at least about 6, 8, 10, 12, 14, 16, or 18 contiguous complementary nucleotides, including "universal" nucleotides that are complementary to more than one nucleotide partner. Alternatively, a primer, or portion thereof, can hybridize to a primer binding site if there are fewer than 1 or 2 complementarity mismatches over at least about 12, 14, 16, or 18 contiguous complementary nucleotides. In some embodiments, the defined temperature at which specific hybridization occurs is room temperature. In some embodiments, the defined temperature at which specific hybridization occurs is higher than room temperature. In some embodiments, the defined temperature at which specific hybridization occurs is at least about 37, 40, 42, 45, 50, 55, 60, 65, 70, 75, or 80° C.

As used herein, "nucleic acid" refers to DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, points of attachment and functionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications including but not limited to capping with a fluorophore (e.g., quantum dot) or another moiety.

As used herein, the term "partitioning" or "partitioned" refers to separating a sample into a plurality of portions, or "partitions." Partitions can be solid or fluid. In some embodiments, a partition is a solid partition, e.g., a microchannel or a well (i.e., in a multi-well microtiter dish). In some embodiments, a partition is a fluid partition, e.g., a droplet. In some embodiments, a fluid partition (e.g., a droplet) is a mixture of immiscible fluids (e.g., water and oil). In some embodiments, a fluid partition (e.g., a droplet) is an aqueous droplet that is surrounded by an immiscible carrier fluid (e.g., oil).

As used herein, a "barcode" is a short nucleotide sequence (e.g., at least about 4, 6, 8, 10, 12, 14, 16, 18, 20, 25, 30 or more nucleotides long) that identifies a molecule to which it is conjugated. In some embodiments, a barcode is used to identify molecules in a partition. Such a partition-specific barcode can be unique for that partition as compared to barcodes present in other partitions, though as explained herein with some frequency two or more barcodes can occur in the same partition. In one example, partitions containing target RNA from single cells can be subjected to reverse transcription conditions using primers that contain a different partition-specific barcode sequence in a majority of partitions, thus incorporating a copy of a unique "cellular barcode" into the reverse transcribed nucleic acids of partitions. Thus, nucleic acid from each cell can be distinguished from nucleic acid of other cells due to the unique "cellular barcode." In some embodiments, a barcode is present on oligonucleotides conjugated to a particle, wherein the "particle barcode" is shared by (e.g., identical or substantially identical amongst) all, or substantially all, of the oligonucleotides conjugated to that particle.

DETAILED DESCRIPTION OF THE INVENTION

Introduction

Figure 4:
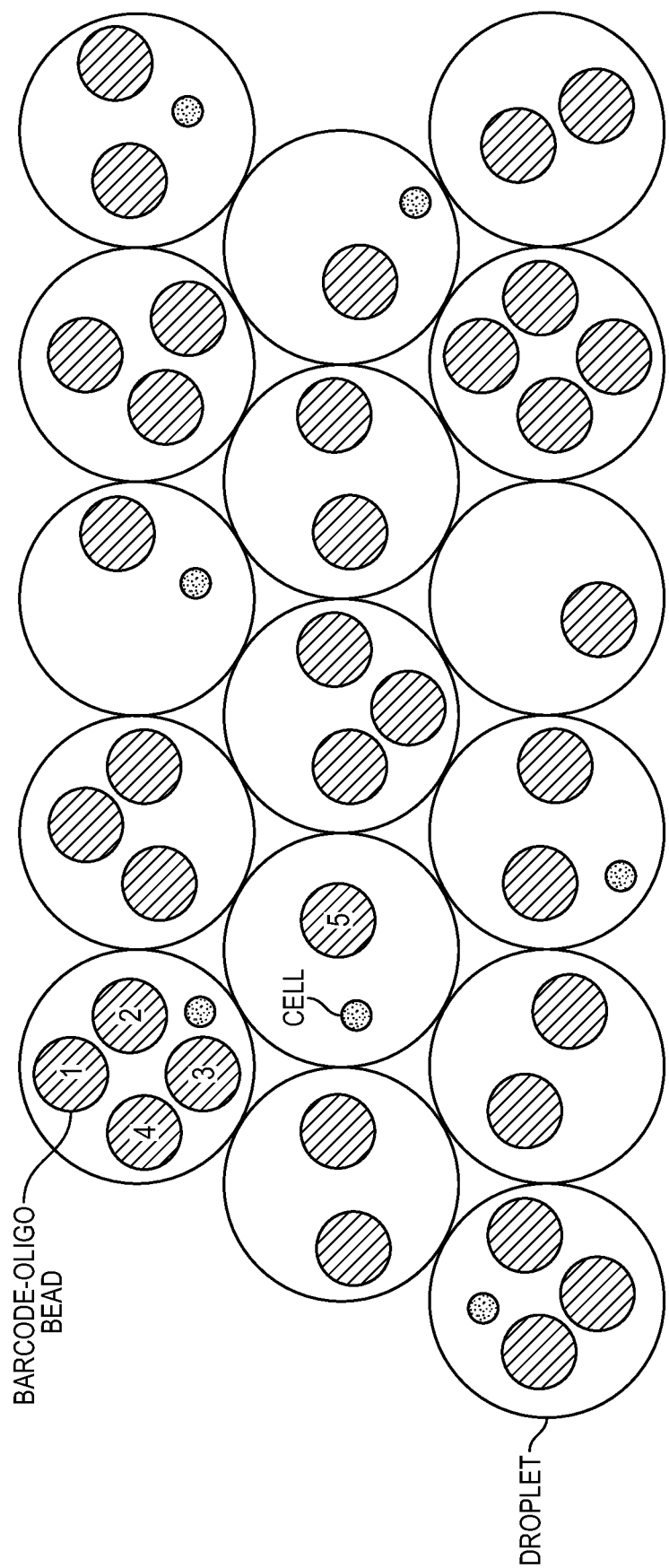
FIG. 4 illustrates an example of delivery of cells and beads carrying barcodes to partitions (or formation of partitions from a solution containing cells and beads) results in a mixture of partitions that contain a variety of numbers of beads. The number of cells delivered to partitions is generally kept low (indicated here by many partitions lacking any cells) to avoid multiple cells in partitions. To utilize as many partitions as possible the number of beads delivered of partitions results in some cases to multiple beads per partition.

The inventors have discovered a new method of analyzing the sequencing data generated from sequencing sample preparation reactions in partitions, where barcodes for separate partitions are used to "mark" sequence reads as being from separate partitions. When a partition (e.g., a droplet in an emulsion) has more than one barcode (for example due to the random nature of barcode introduction, some partitions contain two or more barcodes), some of the sample nucleic acids are distributed exclusively between (e.g., linked to) the two or more barcodes and some of the sequences are shared by two or more barcodes. See, e.g., FIG. 4. Sequencing is performed in bulk (i.e., the contents of partitions are combined) such that one has not been able to distinguish differently-barcoded sequence reads from different partitions compared to sequence reads from two different barcodes in the same partition. The inventors have discovered how to distinguish such sequence reads, making use of fragmentation that occurred previously (for example, in bulk before partitioning) or other sources of randomness that is introduced into partitions such that partitions contain a different random "signature." For example, the inventors have discovered that the percent overlap of identical fragments between differently-barcoded sequencing reads can be used to determine whether the sequences are from the same or different partition. This method can be applied using the template DNA (i.e., the target DNA whose sequence is desired) itself as a "signature", e.g., where the DNA is randomly fragmented or otherwise brings a source of randomness (e.g., methylation signature), or using an exogenous source of DNA that is introduced into the partitions (e.g., randomly fragmented DNA different from and distinguishable for the template DNA).

For example, in the situation where two barcodes are in the same partition and the sample nucleic acids are fragmented in the partition, each of the different barcodes will be linked to some identical sample nucleic acid fragments. In the alternative situation where barcodes are in different partitions, where the DNA in each partition has a different set of fragmented DNA, the percent of common identical fragments will be much less (a background level common for most pairwise comparisons of sequence reads from different barcodes). Thus, by determining the percent of common fragments having different barcodes and comparing the determined percentage to a threshold value, one can distinguish between these two situations. Once sequence reads from two barcodes have been determined to originate from the same partition, one can then generate a nucleotide sequence for the template in the partition, taking that information into account. As non-limiting examples, one can choose to discard all data where more than one barcode were in the same partition, or one can merge the sequencing read data from the two barcodes, interpreting it all as being from one partition.

Further, it has been discovered that data generated from a plurality of partitions containing more than one barcode can improve sequencing data quality. For example, it has been discovered that increasing the average number of barcodes per partition to two or more can improve rather than harm signal-to-noise ratios for sequencing reads. Thus, for example, one can generate partitions in which at least 10%, 20%, 30%, 40%, 50%, 60%, or 70% of partitions contain two or more different barcodes (different in this context meaning having different nucleotide sequences).

Figure 3:
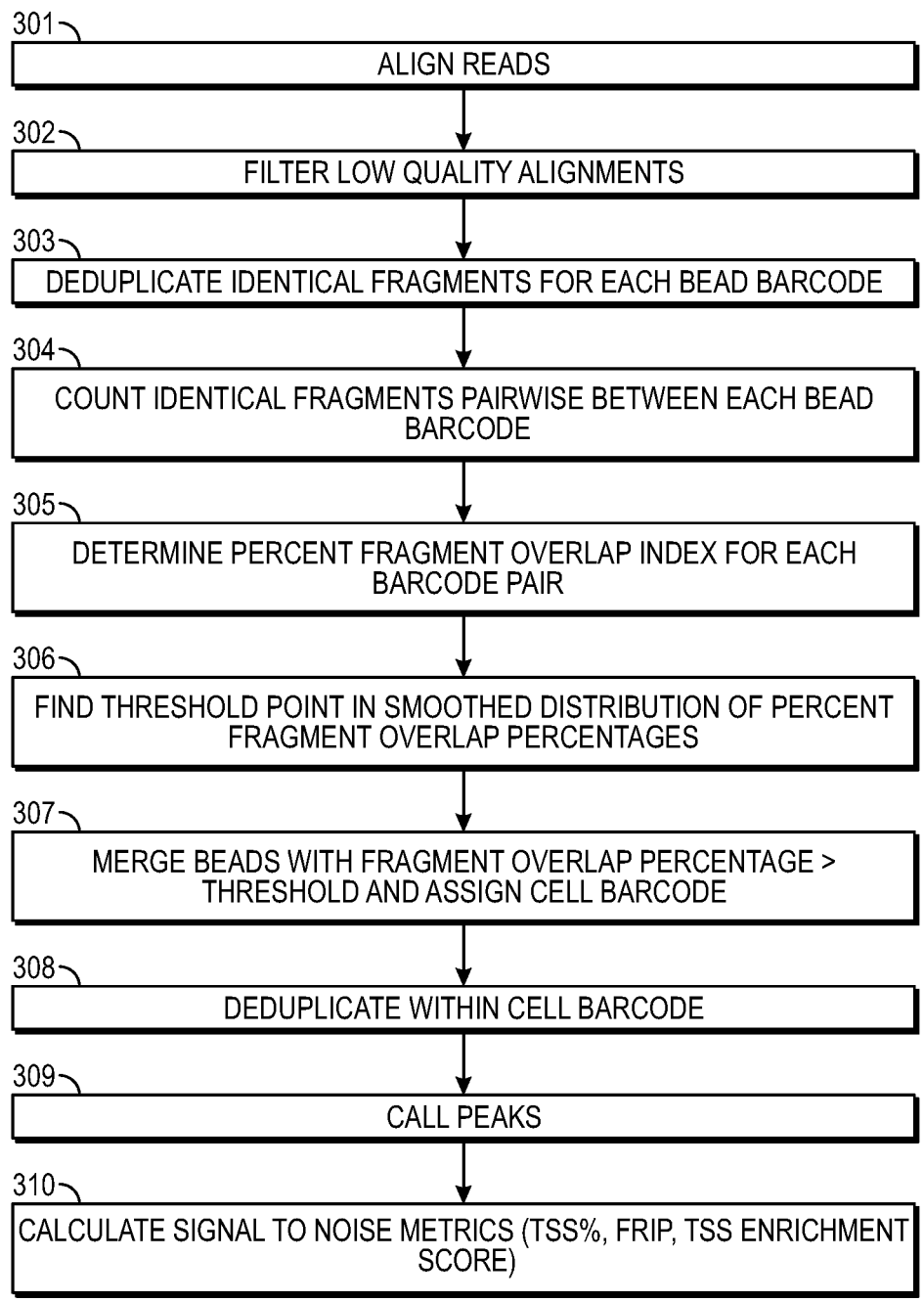
FIG. 3 illustrates an exemplary workflow for identifying and using data from multiple partition barcodes in the same partition.

An exemplary workflow is depicted in FIG. 3. For example, sequencing reads can be aligned (301). Optionally, low quality alignments can be filtered (i.e., removed) (302). Duplicate reads having the same barcodes can be removed so that only one read copy for a particular barcode is provided (303). Identical fragments are determined in a pairwise manner between each bead barcode and counted (304). A percent fragment overlap can be determined for each barcode pair (305). The determined fragment overlap percentage is compared to a threshold value. In some embodiments, the threshold value is determined based upon a smoothed distribution of percent fragment overlap percent among all pairwise comparisons (306). Where percent fragment overlap exceeds the threshold value, reads with different bead barcodes are merged and assigned a partition barcode (307). In some embodiments, one can deduplicate reads within the cell barcode (308), i.e., where identical reads were common for different bead barcodes within a single partition. The resulting sequencing reads can be used to call peaks (309), i.e., identifying areas in a genome that have been enriched with aligned reads (for example as a consequence of performing ATACseq or other sequencing methods). Optionally, one can calculate one or more signal to noise metrics, for example TSS %, FRIP, or TSS Enrichment Score or a combination thereof (310).

Partitioning Samples

Methods and compositions for partitioning are described, for example, in published patent applications WO 2010/036352, US 2010/0173394, US 2011/0092373, and US 2011/0092376. The plurality of partitions can be in a plurality of emulsion droplets, or a plurality of microwells, etc.

In some embodiments, one or more reagents are added during droplet formation or to the droplets after the droplets are formed. Methods and compositions for delivering reagents to one or more partitions include microfluidic methods as known in the art; droplet or microcapsule combining, coalescing, fusing, bursting, or degrading (e.g., as described in U.S. 2015/0027,892; US 2014/0227,684; WO 2012/149,042; and WO 2014/028,537); droplet injection methods (e.g., as described in WO 2010/151,776); and combinations thereof.

As described herein, the partitions can be picowells, nanowells, or microwells. The partitions can be pico-, nano-, or micro-reaction chambers, such as pico, nano, or microcapsules. The partitions can be pico-, nano-, or microchannels. The partitions can be droplets, e.g., emulsion droplets. In some embodiments, a droplet comprises an emulsion composition, i.e., a mixture of immiscible fluids (e.g., water and oil). In some embodiments, a droplet is an aqueous droplet that is surrounded by an immiscible carrier fluid (e.g., oil). In some embodiments, a droplet is an oil droplet that is surrounded by an immiscible carrier fluid (e.g., an aqueous solution). In some embodiments, the droplets described herein are relatively stable and have minimal coalescence between two or more droplets. In some embodiments, less than 0.0001%, 0.0005%, 0.001%, 0.005%, 0.01%, 0.05%, 0.1%, 0.5%, 1%, 2%, 3%, 4%, 5%, 6%, 7%, 8%, 9%, or 10% of droplets generated from a sample coalesce with other droplets. The emulsions can also have limited flocculation, a process by which the dispersed phase comes out of suspension in flakes. In some cases, such stability or minimal coalescence is maintained for up to 4, 6, 8, 10, 12, 24, or 48 hours or more (e.g., at room temperature, or at about 0, 2, 4, 6, 8, 10, or 12° C.). In some embodiments, the droplet is formed by flowing an oil phase through an aqueous sample or reagents.

The oil phase can comprise a fluorinated base oil which can additionally be stabilized by combination with a fluorinated surfactant such as a perfluorinated polyether. In some embodiments, the base oil comprises one or more of a HFE 7500, FC-40, FC-43, FC-70, or another common fluorinated oil. In some embodiments, the oil phase comprises an anionic fluorosurfactant. In some embodiments, the anionic fluorosurfactant is Ammonium Krytox (Krytox-AS), the ammonium salt of Krytox FSH, or a morpholino derivative of Krytox FSH. Krytox-AS can be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of Krytox-AS is about 1.8%. In some embodiments, the concentration of Krytox-AS is about 1.62%. Morpholino derivative of Krytox FSH can be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of morpholino derivative of Krytox FSH is about 1.8%. In some embodiments, the concentration of morpholino derivative of Krytox FSH is about 1.62%.

In some embodiments, the oil phase further comprises an additive for tuning the oil properties, such as vapor pressure, viscosity, or surface tension. Non-limiting examples include perfluorooctanol and 1H,1H,2H,2H-Perfluorodecanol. In some embodiments, 1H,1H,2H,2H-Perfluorodecanol is added to a concentration of about 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.25%, 1.50%, 1.75%, 2.0%, 2.25%, 2.5%, 2.75%, or 3.0% (w/w). In some embodiments, 1H,1H,2H,2H-Perfluorodecanol is added to a concentration of about 0.18% (w/w).

In some embodiments, the emulsion can be substantially monodisperse. In other embodiments, the emulsion can be polydisperse. Emulsion dispersity can arise from the method of emulsion formation. For example, microfluidic emulsion formation is typically low polydispersity compared to "salad shaker" emulsion formation, which can be highly polydisperse. Polydispersity can also arise downstream of emulsion formation, such as when droplets of the emulsion fuse together.

In some embodiments, the emulsion is formulated to produce highly monodisperse droplets having a liquid-like interfacial film that can be converted by heating into microcapsules having a solid-like interfacial film; such microcapsules can behave as bioreactors able to retain their contents through an incubation period. The conversion to microcapsule form can occur upon heating. For example, such conversion can occur at a temperature of greater than about 40°, 50°, 60°, 70°, 80°, 90°, or 95° C. During the heating process, a fluid or mineral oil overlay can be used to prevent evaporation. Excess continuous phase oil can be removed prior to heating, or left in place. The microcapsules can be resistant to coalescence and/or flocculation across a wide range of thermal and mechanical processing.

Following conversion of droplets into microcapsules, the microcapsules can be stored at about −70°, −20°, 0°, 3°, 4°, 5°, 6°, 7°, 8°, 9°, 10°, 15°, 20°, 25°, 30°, 35°, or 40° C. In some embodiments, these capsules are useful for storage or transport of partition mixtures. For example, samples can be collected at one location, partitioned into droplets containing enzymes, buffers, and/or primers or other probes, optionally one or more polymerization reactions can be performed, the partitions can then be heated to perform microencapsulation, and the microcapsules can be stored or transported for further analysis.

In some embodiments, the sample is partitioned into, or into at least, 500 partitions, 1000 partitions, 2000 partitions, 3000 partitions, 4000 partitions, 5000 partitions, 6000 partitions, 7000 partitions, 8000 partitions, 10,000 partitions, 15,000 partitions, 20,000 partitions, 30,000 partitions, 40,000 partitions, 50,000 partitions, 60,000 partitions, 70,000 partitions, 80,000 partitions, 90,000 partitions, 100,000 partitions, 200,000 partitions, 300,000 partitions, 400,000 partitions, 500,000 partitions, 600,000 partitions, 700,000 partitions, 800,000 partitions, 900,000 partitions, 1,000,000 partitions, 2,000,000 partitions, 3,000,000 partitions, 4,000,000 partitions, 5,000,000 partitions, 10,000,000 partitions, 20,000,000 partitions, 30,000,000 partitions, 40,000,000 partitions, 50,000,000 partitions, 60,000,000 partitions, 70,000,000 partitions, 80,000,000 partitions, 90,000,000 partitions, 100,000,000 partitions, 150,000,000 partitions, or 200,000,000 partitions.

In some embodiments, the droplets that are generated are substantially uniform in shape and/or size. For example, in some embodiments, the droplets are substantially uniform in average diameter. In some embodiments, the droplets that are generated have an average diameter of about 0.001 microns, about 0.005 microns, about 0.01 microns, about 0.05 microns, about 0.1 microns, about 0.5 microns, about 1 microns, about 5 microns, about 10 microns, about 20 microns, about 30 microns, about 40 microns, about 50 microns, about 60 microns, about 70 microns, about 80 microns, about 90 microns, about 100 microns, about 150 microns, about 200 microns, about 300 microns, about 400 microns, about 500 microns, about 600 microns, about 700 microns, about 800 microns, about 900 microns, or about 1000 microns. In some embodiments, the droplets that are generated have an average diameter of less than about 1000 microns, less than about 900 microns, less than about 800 microns, less than about 700 microns, less than about 600 microns, less than about 500 microns, less than about 400 microns, less than about 300 microns, less than about 200 microns, less than about 100 microns, less than about 50 microns, or less than about 25 microns. In some embodiments, the droplets that are generated are non-uniform in shape and/or size.

In some embodiments, the droplets that are generated are substantially uniform in volume. For example, the standard deviation of droplet volume can be less than about 1 picoliter, 5 picoliters, 10 picoliters, 100 picoliters, 1 nL, or less than about 10 nL. In some cases, the standard deviation of droplet volume can be less than about 10-25% of the average droplet volume. In some embodiments, the droplets that are generated have an average volume of about 0.001 nL, about 0.005 nL, about 0.01 nL, about 0.02 nL, about 0.03 nL, about 0.04 nL, about 0.05 nL, about 0.06 nL, about 0.07 nL, about 0.08 nL, about 0.09 nL, about 0.1 nL, about 0.2 nL, about 0.3 nL, about 0.4 nL, about 0.5 nL, about 0.6 nL, about 0.7 nL, about 0.8 nL, about 0.9 nL, about 1 nL, about 1.5 nL, about 2 nL, about 2.5 nL, about 3 nL, about 3.5 nL, about 4 nL, about 4.5 nL, about 5 nL, about 5.5 nL, about 6 nL, about 6.5 nL, about 7 nL, about 7.5 nL, about 8 nL, about 8.5 nL, about 9 nL, about 9.5 nL, about 10 nL, about 11 nL, about 12 nL, about 13 nL, about 14 nL, about 15 nL, about 16 nL, about 17 nL, about 18 nL, about 19 nL, about 20 nL, about 25 nL, about 30 nL, about 35 nL, about 40 nL, about 45 nL, or about 50 nL.

In some embodiments, the method comprises partitioning a sample comprising one or more target nucleic acids into a plurality of partitions. In some embodiments, the sample comprising target nucleic acids comprises DNA, RNA, or a combination or hybrid thereof. In some embodiments, the sample comprising target nucleic acids comprises genomic DNA or DNA from a subset of a genome (e.g., selected genes that may harbor mutations for a particular population, such as individuals who are predisposed for a particular type of cancer). In some embodiments, the sample comprises contiguity preserved genomic DNA that has been fragmented but retain contiguity by linkage of a protein (e.g., a Tn5 transposase (tagmentase)) to the DNA fragment ends. In some embodiments, the sample comprising target nucleic acids comprises cDNA. In some embodiments, the sample comprising target nucleic acids comprises exome DNA (i.e., a subset of whole genomic DNA enriched for transcribed sequences which contains the set of exons in a genome) or transcriptome DNA (i.e., the set of all mRNA or "transcripts" produced in a cell or population of cells). In some embodiments, the sample comprising target nucleic acids comprises long fragment DNA (e.g., DNA having a length of at least about 300, 400, 500, 600, 700, 800, 1000, or more bases, or base pairs for double-stranded DNA). In some embodiments, the sample comprising target nucleic acids comprises RNA, e.g., mRNA or lncRNA. In some embodiments, the target nucleic acids are double stranded. In some embodiments, the target nucleic acids are single stranded. In some embodiments, the sample comprises target nucleic acids that are isolated from tissue or cells. In some embodiments, the sample comprises target nucleic acids situated in single cell or single nuclei.

In some embodiments, the sample comprising target nucleic acids is a biological sample. Biological samples can be obtained from any biological organism, e.g., an animal, plant, fungus, pathogen (e.g., bacteria or virus), or any other organism. In some embodiments, the biological sample is from an animal, e.g., a mammal (e.g., a human or a non-human primate, a cow, horse, pig, sheep, cat, dog, mouse, or rat), a bird (e.g., chicken), or a fish. A biological sample can be any tissue or bodily fluid obtained from the biological organism, e.g., blood, a blood fraction, or a blood product (e.g., serum, plasma, platelets, red blood cells, and the like), sputum or saliva, tissue (e.g., kidney, lung, liver, heart, brain, nervous tissue, thyroid, eye, skeletal muscle, cartilage, or bone tissue); cultured cells, e.g., primary cultures, explants, and transformed cells, stem cells, stool, urine, etc. In some embodiments, the sample is a sample comprising cells. In some embodiments, the sample is a single-cell sample.

In some embodiments, the methods described herein are used for single cell analysis. Accordingly, in some embodiments, target nucleic acids from a single cell are partitioned into a plurality of partitions. In some embodiments, single cells are delivered to the individual partitions. In some embodiments, target nucleic acids from a biological sample containing a plurality of cells or nuclei are extracted and partitioned such that individual partitions contain nucleic acid from less than one, one, or a plurality of cells or nuclei. A cell itself is not required to be delivered to partitions provided that nucleic acids from a cell are kept together as a physical entity. This can be achieved by, for example, by fixing cells (e.g., through paraformaldehyde or methanol fixation), embedding the cells in a hydrogel matrix whereby the pore size of the matrix is sufficiently small to prevent diffusion of the target nucleic acids, and capturing the full complement of the target nucleic acids onto a single solid support entity (either one particle (e.g., a magnetic bead) or multiple particles that are bound together).

Barcodes and Beads (Particles)

In some embodiments, nucleic acid barcodes are added to partitions such that relatively few (e.g., on average fewer than 10, fewer than 5, 1-5, 0.5-5) different barcodes (barcodes having different sequences) are in each partition. In some embodiments, multiple copies (e.g., at least 100, e.g., 100-100,000 or $10^7$ or $10^8$ or $10^9$ or more) of a barcode oligo are delivered to each partition. Different particles can be distinguished for example by having different barcodes from one another. This can be achieved, for example, by associating multiple copies of the same barcode oligonucleotide to a bead or other solid support or alternatively containing the multiple copies within a solid or semisolid material that can be delivered to partitions for later optional release of the barcodes in the partitions.

Accordingly, in many cases, it is convenient to deliver to the partitions, or to form the partitions around, a solid support (e.g., a bead) linked to the barcoded oligonucleotide. In some embodiments, a goal of barcode delivery to partitions is a certain (e.g., 1:1) distribution of barcode, or beads linked to oligonucleotides, with partitions. However, due to Poisson distributions, some partitions will contain more than one oligonucleotide (barcoded) bead (also referred herein as a 'particle").

In some embodiments, the barcode is introduced as part of a longer oligonucleotide, for example as a forward oligonucleotide primer comprising the barcode sequence and a 3' capture sequence allowing for hybridization to a target same sequence. In these embodiments, the partitions will include a forward primer for amplification or other linking method (e.g. ligation) of a target nucleic acid. In some embodiments, the forward primer is linked to a bead or other solid support when provided in partitions. Due to statistical distributions, while many partitions will contain only one forward primer (or multiple copies of only one forward primer) linked to one bead, other partitions will include forward primers having different sequences (e.g., different barcodes) as a result of multiple beads being present in at least some partitions. In some embodiments, the bead comprises a solid support surface having a plurality of oligonucleotide primers conjugated thereon. In some embodiments, the bead comprises at least about 10, 50, 100, 500, 1000, 5000, 10,000, 50,000, 100,000, 500,000, 1,000,000, 5,000,000, 10,000,000, $10^8$, $10^9$, $10^{10}$ or more identical forward primers conjugated thereto. In some embodiments, the forward primers are double-stranded. In some embodiments, the forward primers are single-stranded.

In some embodiments, the bead (particle) is a hydrogel bead. In some cases, the hydrogel is in sol form. In some cases, the hydrogel is in gel form. An exemplary hydrogel is an agarose hydrogel. Other hydrogels include, but are not limited to, those described in, e.g., U.S. Pat. Nos. 4,438,258; 6,534,083; 8,008,476; 8,329,763; U.S. Patent Appl. Nos. 2002/0,009,591; 2013/0,022,569; 2013/0,034,592; and International Patent Publication Nos. WO/1997/030092; and WO/2001/049240. For example, the particle can be a hydrogel or other gel bead that contains oligonucleotides that can subsequently be released by melting or dissolving the particle.

The solid support surface of the bead can be modified to include a linker for attaching barcode oligonucleotides. The linkers may comprise a cleavable moiety. Non-limiting examples of cleavable moieties include a disulfide bond, a dioxyuridine moiety, and a restriction enzyme recognition site. Numerous methods for covalently linking an oligonucleotide to one or more hydrogel matrices are known in the art. As but one example, aldehyde derivatized agarose can be covalently linked to a 5'-amine group of a synthetic oligonucleotide. In some embodiments, the oligonucleotide configured to link the hydrogel to the barcode is conjugated to a high molecular weight (e.g., at least about 5, 10, 15, 20, 25, 30, 35, 40, 50 kDa, or more) polymer that can be sterically constrained within a gel form hydrogel matrix. For example, the oligonucleotide can be conjugated to a high molecular weight linear or branched polyacrylamide. As another example, the oligonucleotide can be conjugated to a high molecular weight nucleic acid. The high molecular weight polymer oligonucleotide conjugate (e.g., linear polyacrylamide oligonucleotide conjugate) can be incorporated into a hydrogel matrix by mixing with sol hydrogel and hardening the hydrogel into gel form. In some cases, the plurality of the partitions contain an oligonucleotide conjugated to a high molecular weight linear or branched polyacrylamide, a hydrogel in sol form, and a bifunctional barcode template containing a unique partition-specific barcode. Other high molecular weight polymers are suitable for conjugation with an oligonucleotide and encapsulation into a hydrogel. Exemplary polymers include, but are not limited to, dextrans, chitosan, styrenated gelatin, hyaluronic acid, alginate, gelatin, polyethylene glycols, and derivatives thereof.

Number of Barcodes Per Partition

The present disclosure demonstrates at least two different aspects. First, that the occurrence of multiple sequence-different barcodes in a partition can be detected by determining the percent of common identical fragments, or other feature distinguishable between partitions due to partition-specific randomness, having different barcodes and comparing that determined percent to a threshold so that sequence reads having different barcodes that occurred in the same partition can be detected. Second, it has been discovered that in some embodiments it can improve sequencing data to generate sequencing data from partitions having on average more than one sequence-different barcode per partition.

The average number of sequence-different barcodes per partition, when delivered on beads as described herein, can be predicted by controlling the number of barcoded-beads relative to the number of partitions generated. In some embodiments, the average number of structurally-distinct barcodes (e.g., delivered on beads as described) is between 0.5-1.5 per partition. These might occur for example, when one desires to have as many partitions as possible containing only one structurally-distinct barcode (though with multiple barcode copies of a given species in the partition). In these embodiments, one might use the methods described herein to detect and address data from partitions containing more than one structurally-distinct barcodes. In other embodiments, the average number of structurally-distinct barcodes (e.g., delivered on beads as described) is more than one, for example between 1-5, or 1-2, or 2-5 or more. In these embodiments, one can use any method available (including but not limited to the method described herein of determining the percent of common fragments having different barcodes and comparing that determined percent to a threshold) to deconvolute sequence reads having different barcodes, but with improved sequencing performance (e.g., improved signal-to-noise).

Following formation of the partitions containing at least one barcoded primer, one can perform molecular methods for detection of a target nucleic acid in the partitions. Thus, in many embodiments, sample nucleic acids are also in the partition. Exemplary molecular methods can include any molecular method for detecting nucleic acids, including but not limited to, template-based primer extension (e.g., polymerase chain reaction) or methods that detect specific hybridization to a target nucleic acid via the forward primer capture sequence. In some embodiments, the method comprises ligation. Any of these molecular methods can be performed while the partitions are intact, or after the contents of the partitions have been merged (such that the methods are performed "in bulk").

DNA Template Fragmentation

Some of the methods described herein comprise providing DNA template fragments in partitions. DNA template fragments can be generated as desired. For example, fragments can be generated by shearing or other physical force or by enzymatic cleavage. An increasingly common method of generating DNA fragments for sequencing involves contacting a DNA template with a modified transposase (sometimes referred to as a tagmentase) that cleaves DNA and introduces a short adaptor sequence to the ends of the fragments, thereby providing a primer binding sequence that can be used in downstream molecular biology reactions involving, for example, hybridization and amplification and/or ligation.

Heteroadapter-loaded tagmentases and homoadapter-loaded tagmentases can be used as described herein. Homoadapter-loaded tagmentases are tagmentases that contain adaptors of only one sequence, which adaptor is added to both ends of a tagmentase-induced breakpoint in the genomic DNA. Heteroadapter loaded tagmentases are tagmentases that contain two different adaptors, such that a different adaptor sequence is added to the two DNA ends created by a tagmentase-induced breakpoint in the DNA. Adapter loaded tagmentases are further described, e.g., in U.S. Patent Publication Nos: 2010/0120098; 2012/0301925; and 2015/0291942 and U.S. Pat. Nos. 5,965,443; 6,437,109; 7,083,980; 9,005,935; and 9,238,671, the contents of each of which are hereby incorporated by reference in the entirety for all purposes.

A tagmentase is an enzyme that is capable of forming a functional complex with a transposon end-containing composition and catalyzing insertion or transposition of the transposon end-containing composition into the double-stranded target DNA with which it is incubated in an in vitro transposition reaction. Exemplary transposases include but are not limited to modified Tn5 transposases that are hyperactive compared to wildtype Tn5, for example can have one or more mutations selected from E54K, M56A, or L372P. Wild-type Tn5 transposon is a composite transposon in which two near-identical insertion sequences (IS50L and IS50R) are flanking three antibiotic resistance genes (Reznikoff W S. *Annu Rev Genet* 42: 269-286 (2008)). Each IS50 contains two inverted 19-bp end sequences (ESs), an outside end (OE) and an inside end (IE). However, wild-type ESs have a relatively low activity and were replaced in vitro by hyperactive mosaic end (ME) sequences. A complex of the transposase with the 19-bp ME is thus all that is necessary for transposition to occur, provided that the intervening DNA is long enough to bring two of these sequences close together to form an active Tn5 transposase homodimer (Reznikoff W S., *Mol Microbiol* 47: 1199-1206 (2003)). Transposition is a very infrequent event in vivo, and hyperactive mutants were historically derived by introducing three missense mutations in the 476 residues of the Tn5 protein (E54K, M56A, L372P), which is encoded by IS50R (Goryshin I Y, Reznikoff W S. 1998. *J Biol Chem* 273: 7367-7374 (1998)). Transposition works through a "cut-and-paste" mechanism, where the Tn5 excises itself from the donor DNA and inserts into a target sequence, creating a 9-bp duplication of the target (Schaller H. *Cold Spring Harb Symp Quant Biol* 43: 401-408 (1979); Reznikoff W S., *Annu Rev Genet* 42: 269-286 (2008)). In current commercial solutions (Nextera™ DNA kits, Illumina), free synthetic ME adaptors are end-joined to the 5'-end of the target DNA by the transposase (tagmentase). In some embodiments, the tagmentase is linked to a solid support (e.g., a bead that is different from the bead linked to the forward primer). An example commercial bead-linked tagmentase is Nextera™ DNA Flex (Illumina).

In some embodiments, the adaptor(s) is at least 19 nucleotides in length, e.g., 19-100 nucleotides. In some embodiments, the adapters are double stranded with a 5' end overhang, wherein the 5' overhand sequence is different between heteroadaptors, while the double stranded portion (typically 19 bp) is the same. In some embodiments, an adaptor comprises TCGTCGGCAGCGTC (SEQ ID NO:1) or GTCTCGTGGGCTCGG (SEQ ID NO:2). In some embodiments involving the heteroadaptor-loaded tagmentase, the tagmentase is loaded with a first adaptor comprising TCGTCGGCAGCGTC (SEQ ID NO:1) and a second adaptor comprising GTCTCGTGGGCTCGG (SEQ ID NO:2). In some embodiments, the adapter comprises AGATGTGTATAAGAGACAG (SEQ ID NO:3) and the complement thereof (this is the mosaic end and this is the only specifically required cis active sequence for Tn5 transposition). In some embodiments, the adapter comprises TCGTCGGCAGCGTCAGATGTGTATAAGAGACAG (SEQ ID NO:4) with the complement for AGATGTGTATAAGAGACAG (SEQ ID NO:3) or GTCTCGTGGGCTCGGAGATGTGTATAAGAGACAG (SEQ ID NO:5) with the complement for AGATGTGTATAAGAGACAG (SEQ ID NO:3). In some embodiments involving the heteroadaptor-loaded tagmentase, the tagmentase is loaded with a first adaptor comprising TCGTCGGCAGCGTCAGATGTGTATAAGAGACAG (SEQ ID NO:4) with the complement for AGATGTGTATAAGAGACAG (SEQ ID NO:3) and GTCTCGTGGGCTCGGAGATGTGTATAAGAGACAG (SEQ ID NO:5) with the complement for AGATGTGTATAAGAGACAG (SEQ ID NO:3).

In some embodiments, the DNA is a contiguity-preserved tagmented polynucleotide (e.g., DNA) sequence. In contiguity preserved transposition or tagmentation, a transposase (e.g., Tn5 transposase) is used to modify DNA with adaptor sequences while maintaining contiguity of DNA segments. Conditions for preparing contiguity preserved tagmented polynucleotide sequences are known. See, e.g., Amini et al., Nature Genetics, 2014, 46:1343-1349; WO 2016/061517; and U.S. Provisional Patent Application No. 62/436,288; each of which is incorporated by reference herein. Tagmentase has been observed to remain bound to DNA until a detergent such as SDS is added to the reaction (Amini et al. *Nature Genetics* 46(12):1343-1349).

In some embodiments, the transposase is applied to DNA having chromatin (e.g., histones forming nucleosomes and/or comprising other DNA accessory factors that form chromatin). In these embodiments, the transposase will not have equal access to all of the DNA because of the presence of nucleosomes. These methods are sometimes referred to as "Assay for Transposase Accessible Chromatin using sequencing" or "ATAC-seq" (see, e.g., US Patent Publication No. 20160060691; Buenrostro et al. (2015) *Curr Protoc Mol Biol.* 109:21.29.1-21.29.9) and can be used to determine chromatin changes to different conditions, for example. In some embodiments the DNA is contained within its native cell. For example, the native cell can be fixed and permeabilized such that a transposase can enter the nucleus of the cell and cleave the DNA as the chromatin structure allows. This can be considered an assay for transposase accessibility of chromatin. Accordingly, in some embodiments the DNA is in the form of chromatin, for example within cells or isolated nuclei.

In other embodiments, the DNA is substantially free of protein. For example, the DNA sample has been extracted with phenol to remove DNA binding proteins.

The DNA can be partitioned before being fragmented or after fragmentation or fragmentation and partitioning can occur concurrently. For example, in some embodiments, once the DNA sample has been treated with the transposase, the DNA can be formed into a plurality of separate partitions, e.g., droplets.

In some embodiments, instead of, or in combination with the use of template DNA fragmentation, template DNA in partitions can be treated with biochemistries that allow for the detection of cytosine methylation. In one embodiment, the biochemistry used to detect cytosine methylation uses bisulfite treatment where bisulfite alters ("converts") unmethylated cytosines but does not alter methylated cytosines. In another embodiment, the biochemistry used to detect cytosine methylation uses TET-oxidization of methylated cytosines and APOBEC conversion of non-oxidized unprotected cytosines. Methylation (e.g., as detected by bisulfite conversion) can be used as a source of partition-specific randomness where different cells are delivered to different partitions. In this case, a majority of partitions containing cells will contain only one cell. Because each individual cell will have a distinct methylation pattern, resulting in bisulfite-treated or TET-oxidized APOBEC converted DNA will vary between partitions in line with the methylation differences between cells. Cells to be delivered in partitions can be pre-encapsulated in a first partition, such as a droplet or a hydrogel bead, to keep the DNA from single cells physically associated during methyl conversion treatment. Moreover, a lack of 100% efficiency of the methyl-conversion treatment can be used to generate partition-specific randomness by generating different DNA sequences in different partitions (e.g., even if the starting DNA in the partitions is the same due to the lack of perfect efficiency of the bisulfite conversion).

Figure 5:
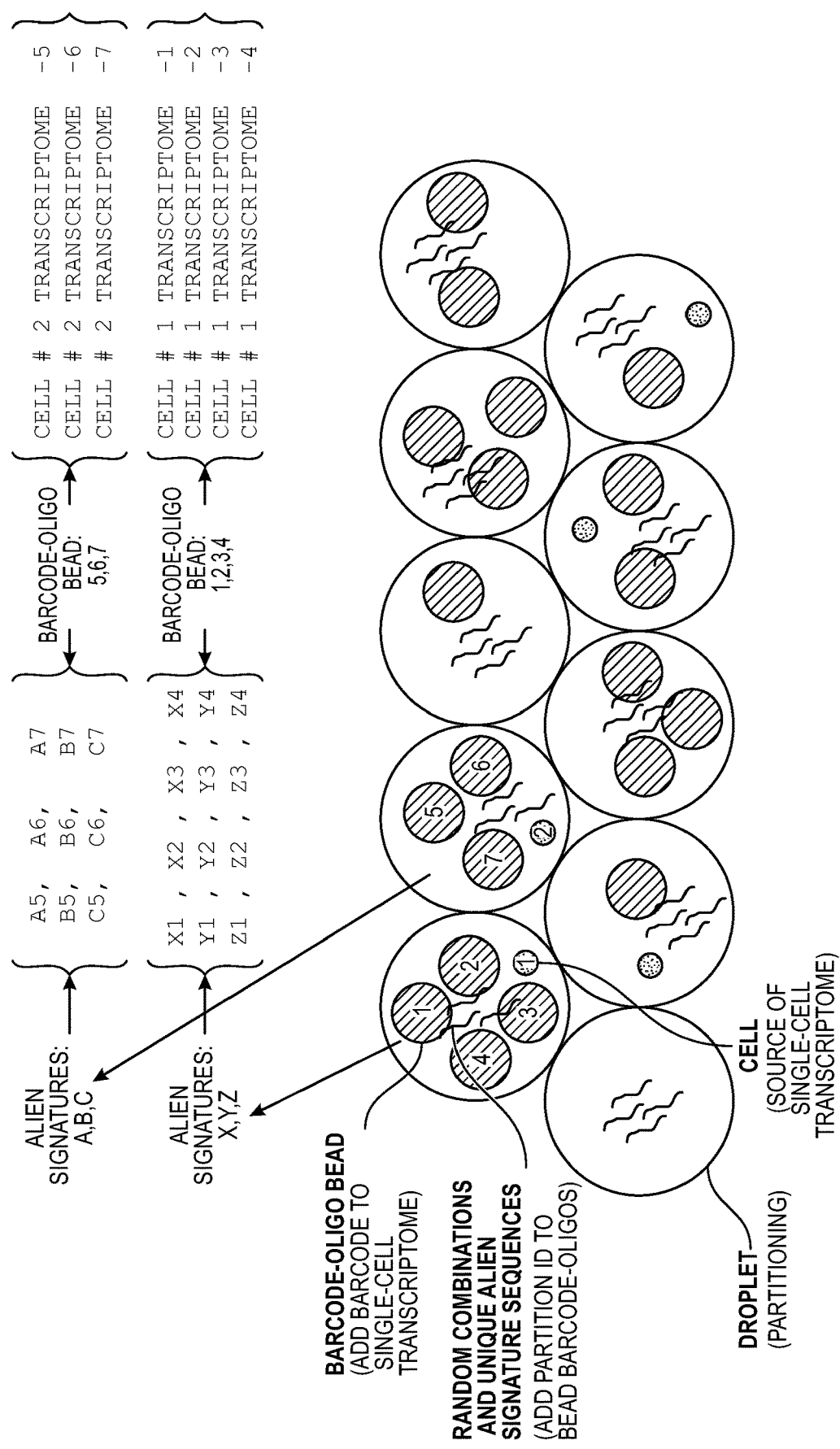
FIG. 5 illustrates how introduction of exogenous (alien) random sequences into partitions generates a partition-specific "signature" of exogenous sequences, which once barcoded with any barcodes in the partition, can be used to associate barcodes from the same partition (because barcodes in the same partition will be associated with the same signature of exogenous fragments.
Figure 6:
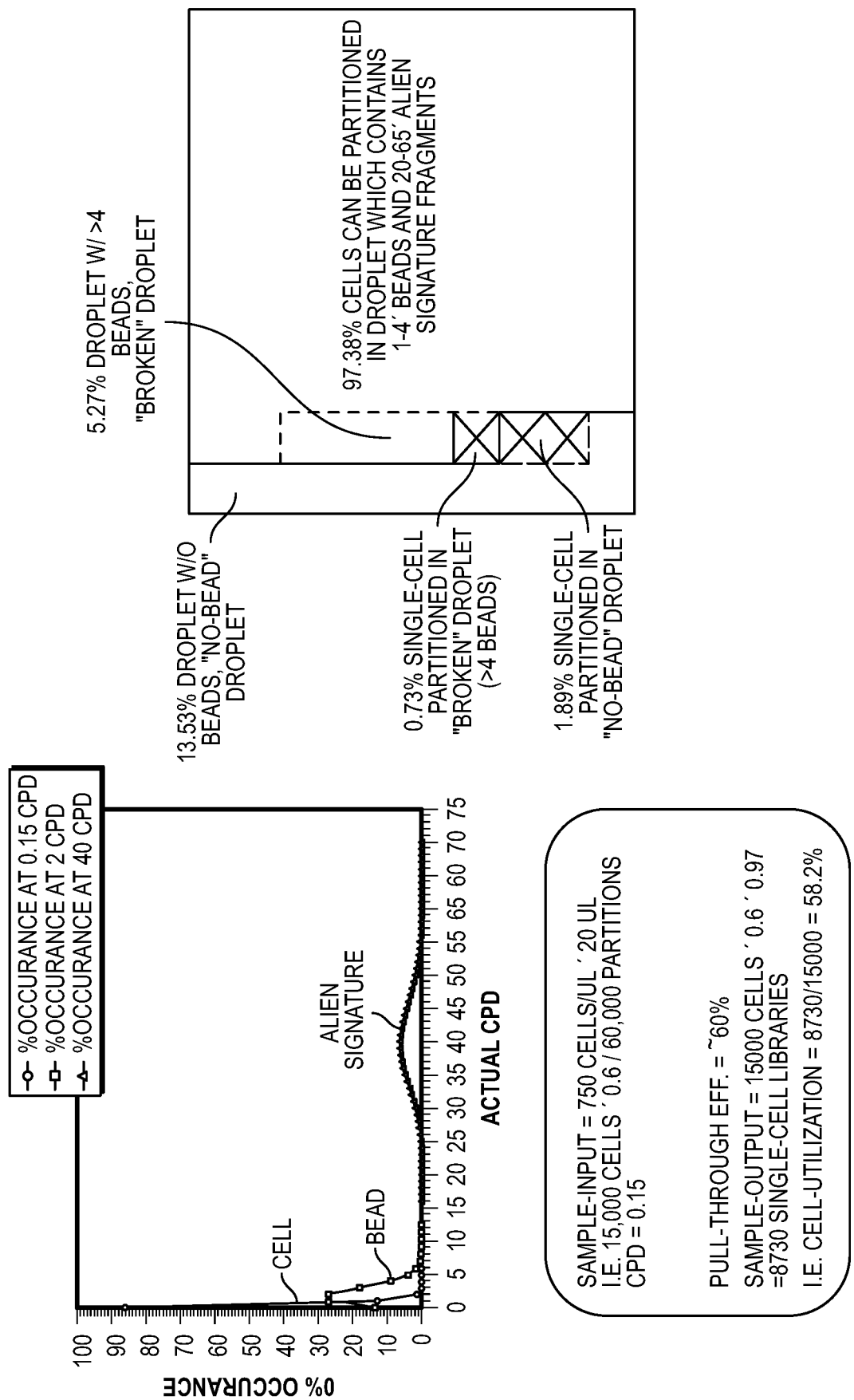
FIG. 6 illustrates a theoretical analysis of distribution of partitioning with cells and barcode-linked beads. The upper left graph displays possible distribution of cells (ideally avoiding partitions containing multiple cells), beads (provided in higher concentration than cells during partition formation, resulting in multiple beads per partition in a number of partitions, and exogenous fragments ("alien signature"), which are provided in a concentration so that different partitions will contain a different mixture of fragments. This distribution is also illustrated at the right of the figure, illustrating a possible set of partitions that can be accessed in view of the signatures described herein.

In other embodiments, the source of partition-specific randomness can be contributed by exogenous molecules (also referred to herein as "alien" molecules) added to the partition or when the partitions are formed. For example, in some embodiments, exogenous DNA (i.e., DNA from a source other than the template DNA) can be randomly-cleaved to generate a plurality of randomly cleaved fragments, with a portion of the fragments added to the partitions. This will result in a unique combination of fragments of the exogenous DNA per partition. By allowing these fragments as well as the template fragments to participate in the barcoding process—e.g., by ligating or extending a portion of bead-specific barcodes with the exogenous fragments—a partition-specific set of exogenous barcoded DNA fragments is generated. By comparing sets of fragments associated with different barcodes, as explained more below, one can determine whether a partition contained more than one bead-specific barcode. See, e.g., FIG. 5.

Figure 7:
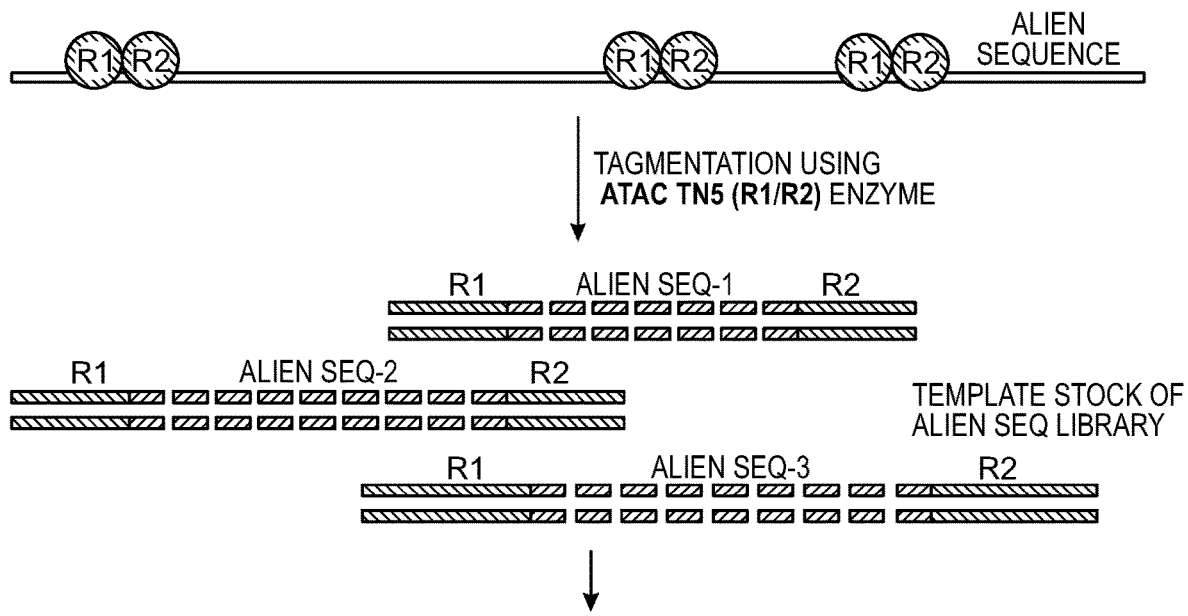
FIG. 7 illustrates one embodiment for generating exogenous DNA fragments. In the embodiment depicted, tagmentation is used to generate random fragments of exogenous DNA. Tagmentation adds adaptor sequences R1 and R2 to the ends of the fragments. The resulting DNA mixture can act as a stock of exogenous sequences one can add to partitions.

The source of exogenous DNA can be any nucleic acid source. In some embodiments, for example, the exogenous DNA is from a cell that is from a different species than the template DNA. Random fragmentation of the exogenous DNA can be achieved by any fragmentation method. In some embodiments, the exogenous DNA is mechanically-sheared or cleaved by an enzyme. Exemplary enzymes include, e.g., any enzyme with DNase or DNA nicking activity. In some embodiments, the enzyme is a transposase such as those described above (e.g., a Tn5 transposase including but not limited to those used in tagmentation) that introduces adaptor sequences to the ends of the resulting fragments. See, e.g., FIG. 7. In yet another alternative, unique exogenous DNA fragments can be generated by gene-synthesis of random sequences, optionally in combination with addition of known adaptors at one or both ends of the fragments.

In one embodiment, the RNA length distribution per cell provides a source of randomness in partitions. This may be an endogenous characteristic of the RNA in any given cell or it may be introduced through exogenously driven RNA fragmentation. The RNA fragmentation can occur prior to partitioning or in the partitions. One possible embodiment is that an adaptor sequence can be added to the 5' end of the RNA molecules through template switching. In another embodiment, the RNA-cDNA hybrid is tagmented during the reverse transcription reaction in partitions providing partition specific cDNA molecules. Bead barcode oligonucleotides then tag the adapted cDNA through primer templated linear amplification or PCR. If multiple beads are present in a droplet, the partition specific unique RNA or cDNA length patterns can be used to ascertain the beads are in the same partition.

In embodiments in which adaptor sequences are introduced to the ends of the DNA template fragments (introduced either by a tagmentase or other method), a 3' capture sequence linked to the barcode (e.g., as delivered on a bead or other solid support) can be selected to hybridize to an adaptor sequence, thereby allowing for linkage of the barcode oligonucleotide to the DNA template fragments. Template-based extension (e.g., polymerase-based amplification) from the barcode oligonucleotide or ligation can for example be used to covalently link the barcode to copies of the DNA template fragments.

Figure 8:
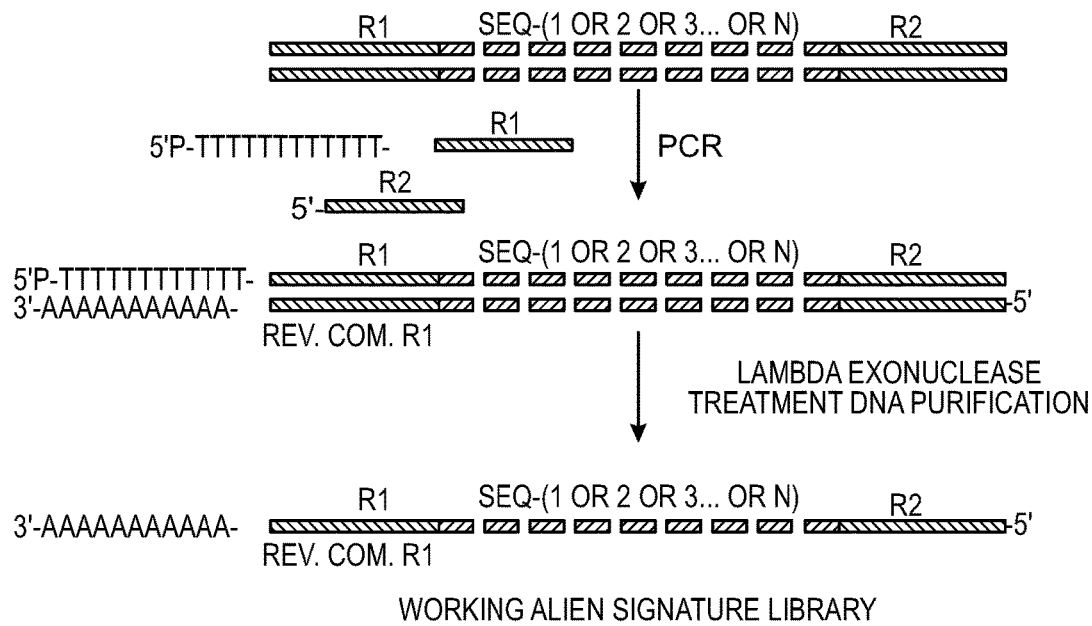
FIG. 8 illustrates continues from FIG. 7 and shows the formation of single-stranded exogenous fragments comprising adaptor sequences as well as an added sequence, which in this case is a polyT sequence, which in turn is rendered to a polyA in the complementary sequence.
Figure 9:
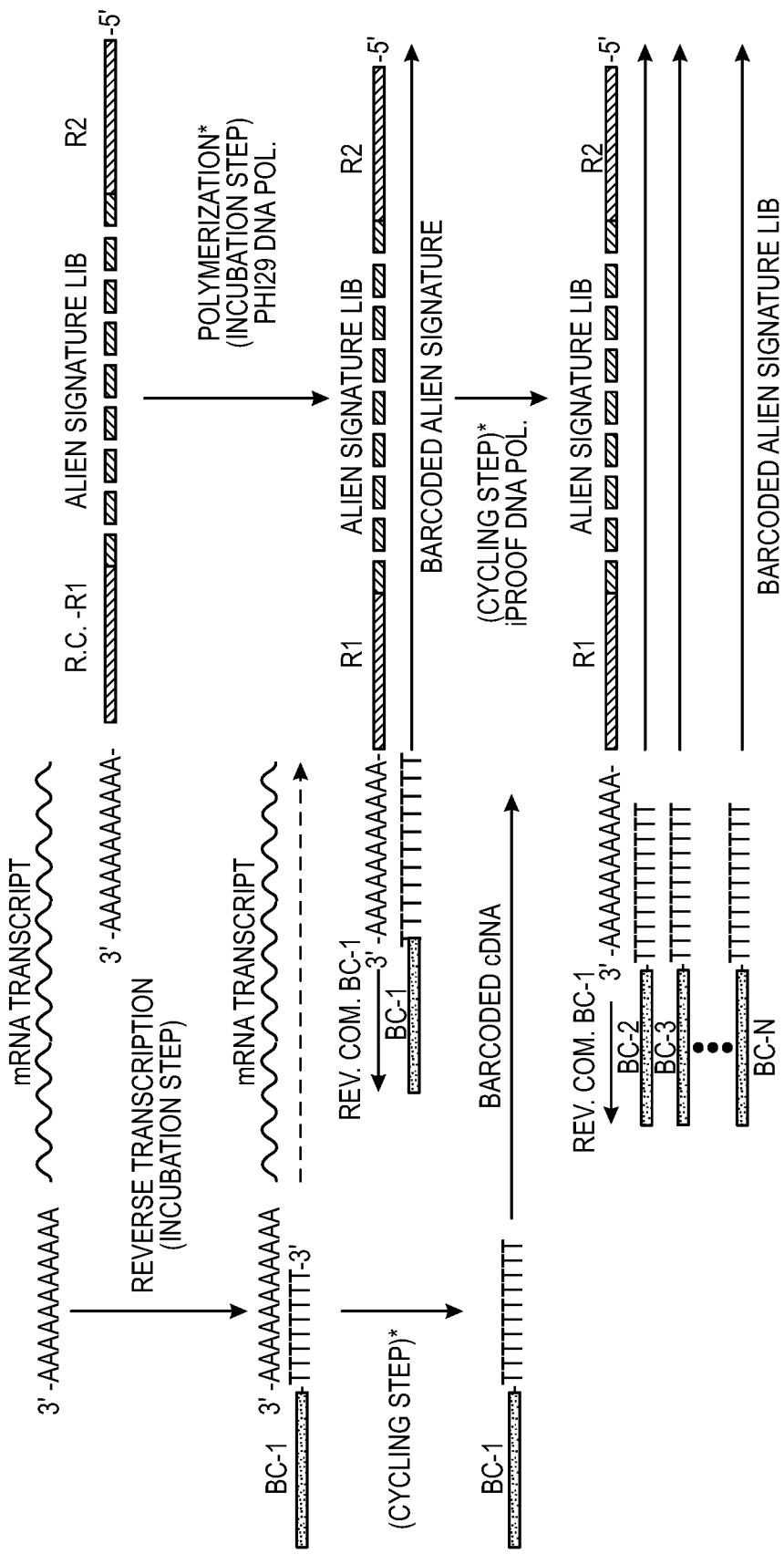
FIG. 9 illustrates a schematic showing a method for introducing barcodes into first strand cDNAs as well as exogenous DNA fragments in partitions (which as a group form a "signature"). As shown, the exogenous fragments have a 3' polyA sequence (e.g., as made in FIGS. 7-8) and are linked to a barcode via hybridization of the 3' capture sequence (poly T) linked to the barcode and the polyT sequence linked to the exogenous DNA fragments. The strands are then extended to form a double-stranded library of barcoded sequences that can be used as a signature for partitions.
Figure 10:
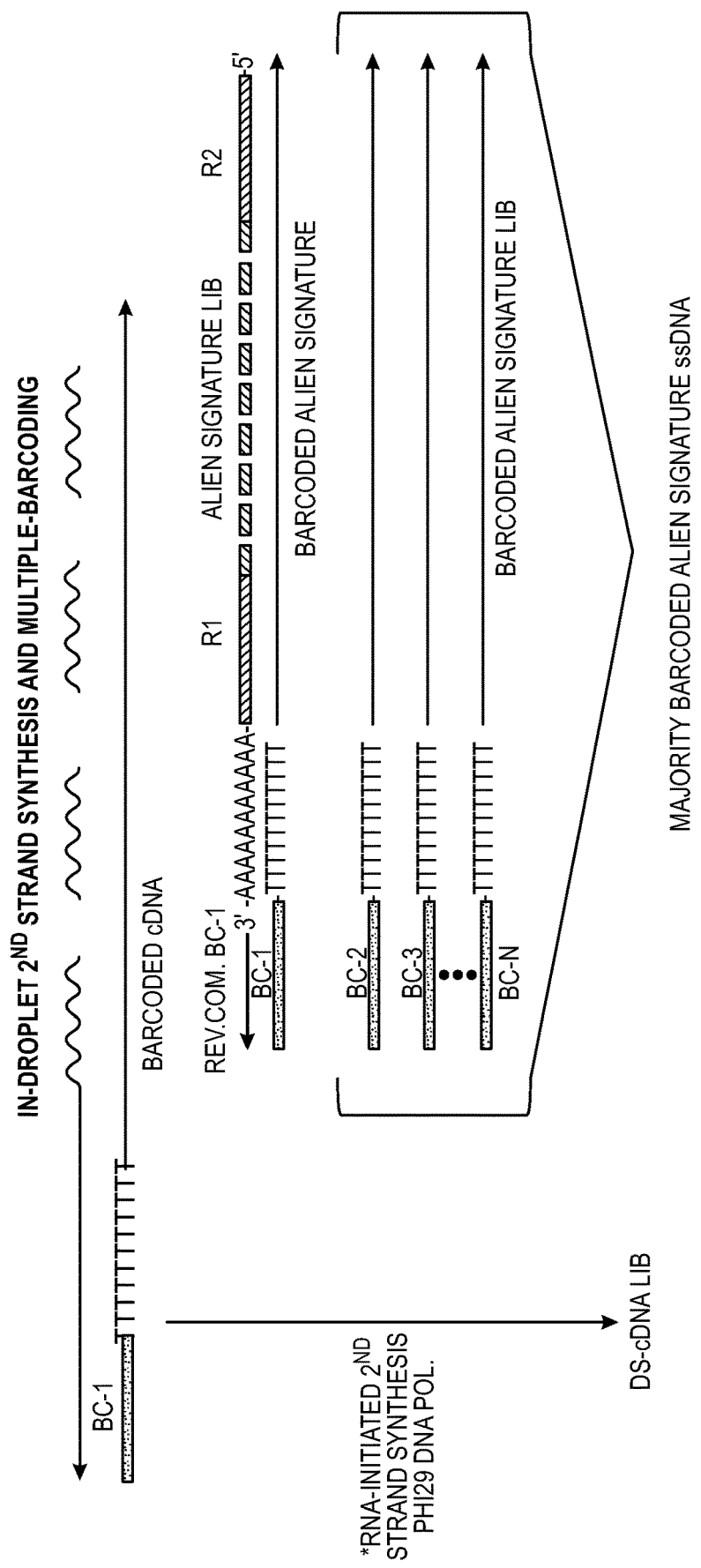
FIG. 10 illustrates contemporaneous formation of cDNA second strands and barcoding of exogenous poly A-containing exogenous DNA to form a signature for partitions.
Figure 11:
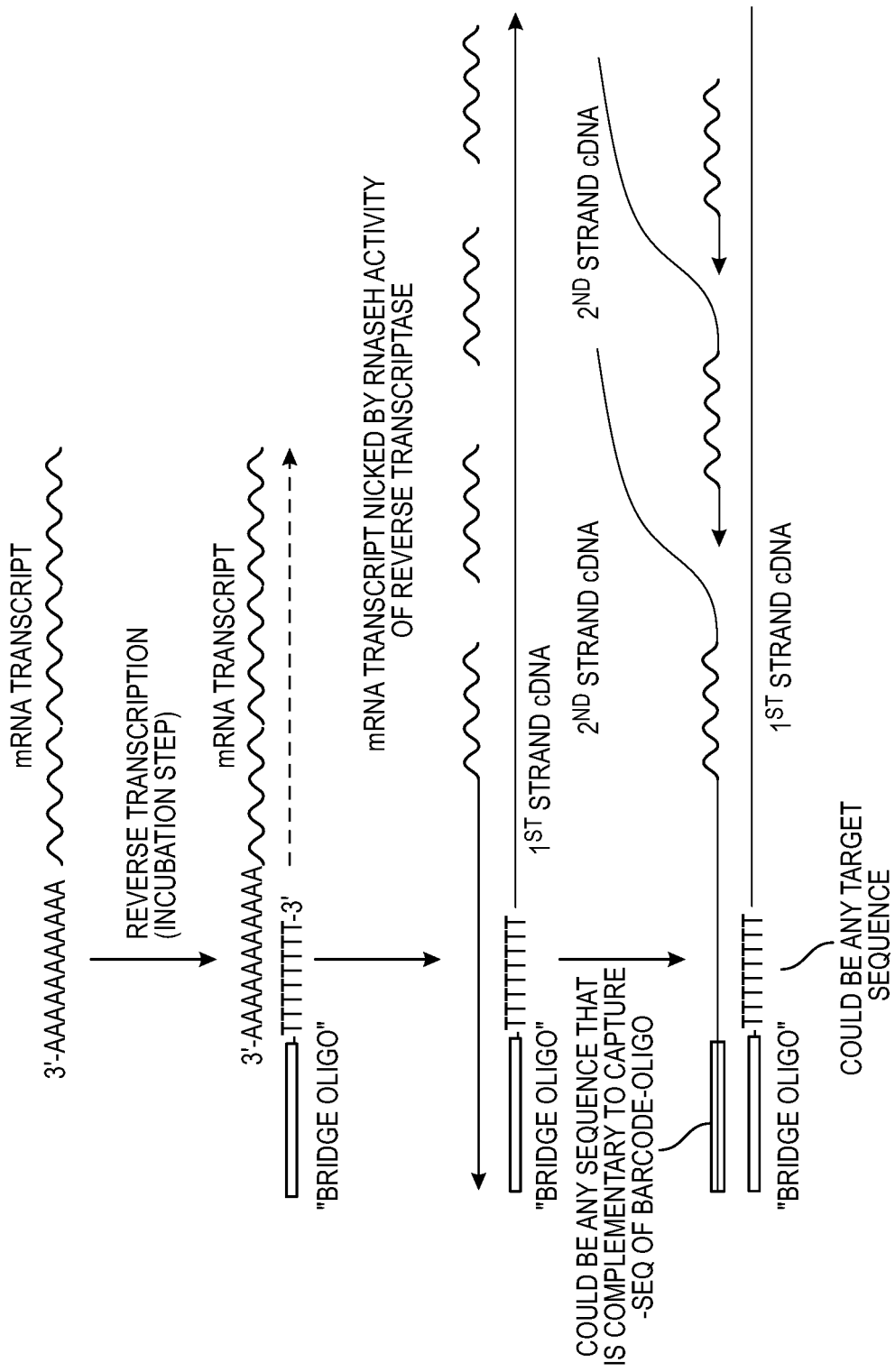
FIG. 11 illustrates, in partitions, reverse transcribing mRNA into first-strand cDNA and then second-strand synthesis using RNaseH activity and multiple-displacement initiated from the nicks. A nucleotide sequence that is complementary to the barcode-oligo capture sequence can be introduced by a bridge-oligonucleotide, which acts as a primer for first-strand cDNA synthesis by reverse transcription. Second strand cDNAs are generated through multiple-displacement so that a second strand end sequence hybridizes to the capture sequence of barcode-oligo, thereby forming a cDNA linked to a barcode.

In some embodiments, the template DNA to be sequenced is cDNA sequence where the cDNAs are generated from RNA in the partitions. In some of these aspects, mRNA is captured by a poly-T sequence (e.g., 5 or 10 or more contiguous Ts) or alternatively a target-specific sequence at the 3' capture sequence linked to the barcode sequence. The exogenous DNA fragments can be incorporated into this process to assist with deconvolution of barcodes. In embodiments where exogenous DNA is used as a source of partition-specific randomness, a polyT sequence or the target-specific sequence can be added to the 5' end of exogenous DNA fragments (optionally that have a known adaptor sequence at the 5' end, 3' end, or both). In one embodiment, once the exogenous DNA fragments have adaptor sequences, the fragments can be amplified in the presence of a primer with the poly-T or target-specific sequence. See, e.g., FIG. 8. A 5' phosphate can be included on the primer such that one strand has a 5' phosphate. The other strand of the double-stranded DNA product produced by amplification will contain a polyA (or complement to the target-specific) sequence. The 5' phosphate-containing strand can be digested, e.g., by lambda exonuclease, leaving a single-strand containing the polyA (or complement to the target-specific) sequence. See, e.g., FIG. 8. This sequence can be subsequently used in the first-strand cDNA synthesis process. See, e.g., FIG. 9. The 3' capture sequence linked to the barcode sequence can be used to primer the first strand cDNA and can also be extended to copy the exogenous (alien) DNA fragments, thereby linking a bead-specific barcode to the exogenous fragment sequences. The resulting products in the partitions are barcoded first strand cDNA and barcoded exogenous DNA fragments. See, FIG. 9. Second-strands of the cDNA as well as the exogenous DNA fragments can be synthesized. For example, in some embodiments, the methods depicted in FIG. 11 can be used.

In some embodiments, the partitions can also contain a second oligonucleotide primer, which can optionally be linked to the bead (particle), or not. This primer can function as a reverse primer for the first oligonucleotide primer such that the two oligonucleotides generate an amplicon in PCR. The second oligonucleotide primer will have a 3' end that is complementary to an adaptor sequence, i.e., the adaptor sequence at the opposite end of the DNA segment compared to the adaptor sequence targeted by the first oligonucleotide primer. In some embodiments, the 3' end will be complementary to the entire adaptor sequence. In some embodiments, at least the 3'-most 6, 7, 8, 9, 10, 11, 12, 13, 14, 15, 16, 17, 18, 19, or 20 of the oligonucleotide are complementary to a sequence in the adaptor. The second oligonucleotide primer can also contain a universal or other additional sequence to assist with downstream manipulation or sequencing of the amplicon. For example, when Illumina-based sequencing is used the second oligonucleotide primer can have a 5' P5 or P7 sequence for binding to the Illumina flow cell (optionally with the first oligonucleotide primer having the other of the two sequences).

Prior to amplification, one can remove, release, or cleave oligonucleotide primer(s) from the bead. This can be achieved by any method as desired. Methods of cleaving include, but are not limited to altering the pH or contacting the oligonucleotides with UDG/ApeI or a restriction endonuclease. In some embodiments, the oligonucleotide is linked to the bead via one or more uracils (Us) and USER enzyme (e.g., from NEB) is used to cleave the Us incorporated in the oligo backbone. USER has 2 enzymes: UDG and Endonuclease VIII. In some cases, the oligonucleotides are attached to a solid support through a disulfide linkage (e.g., through a disulfide bond between a sulfide of the solid support and a sulfide covalently attached to the 5' or 3' end, or an intervening nucleic acid, of the oligonucleotide). In such cases, the oligonucleotide can be cleaved from the solid support by contacting the solid support with a reducing agent such as a thiol or phosphine reagent, including but not limited to a beta mercaptoethanol (BME), dithiothreitol (DTT), or tris(2-carboxyethyl)phosphine (TCEP). It can be advantageous to release the oligonucleotide primer from the bead for a number of reasons. For example, kinetics of DNA interactions will greatly increase. The particle can also be melted or dissolved as described above to release the oligonucleotides.

Amplification can be achieved within the partitions (before combining the contents to the partitions). Various amplification method are known and can be used. Following amplification, the contents of the partitions are combined, processed further as required, i.e. by further amplification and/or DNA fragment size selection and sequenced in bulk. Any method of nucleotide sequencing can be used as desired so long as at least some of the DNA segments sequence and the barcode sequence is determined. Methods for high throughput sequencing and genotyping are known in the art. For example, such sequencing technologies include, but are not limited to, pyrosequencing, sequencing-by-ligation, single molecule sequencing, sequence-by-synthesis (SBS), massive parallel clonal, massive parallel single molecule SBS, massive parallel single molecule real-time, massive parallel single molecule real-time nanopore technology, etc. Morozova and Marra provide a review of some such technologies in *Genomics*, 92: 255 (2008), herein incorporated by reference in its entirety.

Exemplary DNA sequencing techniques include fluorescence-based sequencing methodologies (See, e.g., Birren et al., Genome Analysis: Analyzing DNA, 1, Cold Spring Harbor, N.Y.; herein incorporated by reference in its entirety). In some embodiments, automated sequencing techniques understood in that art are utilized. In some embodiments, the present technology provides parallel sequencing of partitioned amplicons (PCT Publication No.

WO 2006/0841,32, herein incorporated by reference in its entirety). In some embodiments, DNA sequencing is achieved by parallel oligonucleotide extension (See, e.g., U.S. Pat. Nos. 5,750,341; and 6,306,597, both of which are herein incorporated by reference in their entireties). Additional examples of sequencing techniques include the Church polony technology (Mitra et al., 2003, Analytical Biochemistry 320, 55-65; Shendure et al., 2005 Science 309, 1728-1732; and U.S. Pat. Nos. 6,432,360; 6,485,944; 6,511,803; herein incorporated by reference in their entireties), the 454 picotiter pyrosequencing technology (Margulies et al., 2005 Nature 437, 376-380; U.S. Publication No. 2005/0130173; herein incorporated by reference in their entireties), the Solexa single base addition technology (Bennett et al., 2005, Pharmacogenomics, 6, 373-382; U.S. Pat. Nos. 6,787,308; and 6,833,246; herein incorporated by reference in their entireties), the Lynx massively parallel signature sequencing technology (Brenner et al. (2000). Nat. Biotechnol. 18:630-634; U.S. Pat. Nos. 5,695,934; 5,714,330; herein incorporated by reference in their entireties), and the Adessi PCR colony technology (Adessi et al. (2000). Nucleic Acid Res. 28, E87; WO 2000/018957; herein incorporated by reference in its entirety).

Typically, high throughput sequencing methods share the common feature of massively parallel, high-throughput strategies, with the goal of lower costs in comparison to older sequencing methods (See, e.g., Voelkerding et al., Clinical Chem., 55: 641-658, 2009; MacLean et al., Nature Rev. Microbiol., 7:287-296; each herein incorporated by reference in their entirety). Such methods can be broadly divided into those that typically use template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and platforms commercialized by VisiGen, Oxford Nanopore Technologies Ltd., Life Technologies/Ion Torrent, and Pacific Biosciences, respectively.

In pyrosequencing (Voelkerding et al., Clinical Chem., 55: 641-658, 2009; MacLean et al., Nature Rev. Microbiol., 7:287-296; U.S. Pat. Nos. 6,210,891; and 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al., Clinical Chem., 55. 641-658, 2009; MacLean et al., Nature Rev. Microbial., 7:287-296; U.S. Pat. Nos. 6,833,246; 7,115,400; and 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 50 nucleotides, with overall output exceeding 1 billion nucleotide pairs per analytical run.

Sequencing nucleic acid molecules using SOLiD technology (Voelkerding et al., Clinical Chem., 55: 641-658, 2009; MacLean et al., Nature Rev. Microbial., 7:287-296; U.S. Pat. Nos. 5,912,148; and 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, nanopore sequencing is employed (See, e.g., Astier et al., J. Am. Chem. Soc. 2006 Feb. 8; 128(5)1705-10, herein incorporated by reference). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In certain embodiments, HeliScope by Helicos BioSciences is employed (Voelkerding et al., *Clinical Chem.*, 55. 641-658, 2009; MacLean et al., *Nature Rev. Microbial*, 7:287-296; U.S. Pat. Nos. 7,169,560; 7,282,337; 7,482,120; 7,501,245; 6,818,395; 6,911,345; and 7,501,245; each herein incorporated by reference in their entirety). Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (See, e.g., Science 327 (5970): 1190 (2010); U.S. Pat. Appl. Pub. Nos. 2009/0026082; 2009/0127589; 2010/0301398; 2010/0197507; 2010/0188073; and 2010/0137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers the hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per base accuracy of the Ion Torrent sequencer is ~99.6% for 50 base reads, with ~100 Mb generated per run. The read-length is 100 base pairs. The accuracy for homopolymer repeats of 5 repeats in length is ~98%. The benefits of ion semiconductor sequencing are rapid sequencing speed and low upfront and operating costs.

Another exemplary nucleic acid sequencing approach that may be adapted for use with the present invention was developed by Stratos Genomics, Inc. and involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 2009/0035777, which is incorporated herein in its entirety.

Other single molecule sequencing methods include real-time sequencing by synthesis using a VisiGen platform (Voelkerding et al., Clinical Chem., 55: 641-58, 2009; U.S. Pat. No. 7,329,492; and U.S. patent application Ser. Nos. 11/671,956; and 11/781,166; each herein incorporated by reference in their entirety) in which immobilized, primed DNA template is subjected to strand extension using a fluorescently-modified polymerase and florescent acceptor molecules, resulting in detectible fluorescence resonance energy transfer (FRET) upon nucleotide addition.

Another real-time single molecule sequencing system developed by Pacific Biosciences (Voelkerding et al., Clinical Chem., 55. 641-658, 2009; MacLean et al., Nature Rev. Microbiol., 7:287-296; U.S. Pat. Nos. 7,170,050; 7,302,146; 7,313,308; and 7,476,503; all of which are herein incorporated by reference) utilizes reaction wells 50-100 nm in diameter and encompassing a reaction volume of approximately 20 zeptoliters ($10^{-21}$ L). Sequencing reactions are performed using immobilized template, modified phi29 DNA polymerase, and high local concentrations of fluorescently labeled dNTPs. High local concentrations and continuous reaction conditions allow incorporation events to be captured in real time by fluor signal detection using laser excitation, an optical waveguide, and a CCD camera.

In certain embodiments, the single molecule real time (SMRT) DNA sequencing methods using zero-mode waveguides (ZMWs) developed by Pacific Biosciences, or similar methods, are employed. With this technology, DNA sequencing is performed on SMRT chips, each containing thousands of zero-mode waveguides (ZMWs). A ZMW is a hole, tens of nanometers in diameter, fabricated in a 100 nm metal film deposited on a silicon dioxide substrate. Each ZMW becomes a nanophotonic visualization chamber providing a detection volume of just 20 zeptoliters ($10^{-21}$ L). At this volume, the activity of a single molecule can be detected amongst a background of thousands of labeled nucleotides. The ZMW provides a window for watching DNA polymerase as it performs sequencing by synthesis. Within each chamber, a single DNA polymerase molecule is attached to the bottom surface such that it permanently resides within the detection volume. Phospholinked nucleotides, each type labeled with a different colored fluorophore, are then introduced into the reaction solution at high concentrations which promote enzyme speed, accuracy, and processivity. Due to the small size of the ZMW, even at these high concentrations, the detection volume is occupied by nucleotides only a small fraction of the time. In addition, visits to the detection volume are fast, lasting only a few microseconds, due to the very small distance that diffusion has to carry the nucleotides. The result is a very low background.

Processes and systems for such real time sequencing that may be adapted for use with the invention are described in, for example, U.S. Pat. Nos. 7,405,281; 7,315,019; 7,313,308; 7,302,146; and 7,170,050; and U.S. Pat. Pub. Nos. 2008/0212960; 2008/0206764; 2008/0199932; 2008/0199874; 2008/0176769; 2008/0176316; 2008/0176241; 2008/0165346; 2008/0160531; 2008/0157005; 2008/0153100; 2008/0153095; 2008/0152281; 2008/0152280; 2008/0145278; 2008/0128627; 2008/0108082; 2008/0095488; 2008/0080059; 2008/0050747; 2008/0032301; 2008/0030628; 2008/0009007; 2007/0238679; 2007/0231804; 2007/0206187; 2007/0196846; 2007/0188750; 2007/0161017; 2007/0141598; 2007/0134128; 2007/0128133; 2007/0077564; 2007/0072196; and 2007/0036511; and Korlach et al. (2008) "Selective aluminum passivation for targeted immobilization of single DNA polymerase molecules in zero-mode waveguide nanostructures" PNAS 105(4): 1176-81, all of which are herein incorporated by reference in their entireties.

Upon completion of sequencing, sequences can be grouped by same barcode. A pairwise comparison between sequence reads of template fragments having different barcodes can be made. A percent of identical template fragment reads in common out of the total number of fragment reads generated for the two barcodes is determined. Identical fragments can be determined for example, by comparing start and stop sequences (i.e., end portions) of the DNA template fragment portion of different sequencing reads from all fragments that are contained within a partition, wherein identical start sequences and stop sequences of two DNA template fragment sequencing reads indicates the two origin DNA fragments are identical.

As an example to illustrate, consider the following prophetic example showing number of reads of different fragments (the example below is greatly simplified for ease of explanation):

|  | Fragment W | Fragment X | Fragment Y | Fragment Z |
|---|---|---|---|---|
| Barcode A | 15 | 5 | 0 | 30 |
| Barcode B | 10 | 30 | 60 | 0 |

The percent of fragments in common in the example above is 25 fragment W plus 35 fragment X divided by the total number of fragments with barcode A and B (150), i.e., 60/150=40%.

For each pairwise comparison between barcodes, a percent value (shared sequences divided by the total number of sequences for the barcodes being compared times 100) can be generated and compared to a threshold value. The threshold value can represent the percent of fragments that would be expected to occur in common at random, or can be another value that allows one to distinguish a percent of DNA fragments shared between barcodes as a result of two barcodes being in one partition compared to occurring at random. In some embodiments, a threshold is determined by plotting the percent in common among all barcodes in a pairwise fashion and then observing when the percent falls off to a background percentage common between random barcodes. See, e.g., FIG. 12. In some embodiments, if the percent fragments in common between two barcodes is more than 0.5%, 1%, 2% or more than 5% the two barcodes are considered to have originated from the same partition.

A nucleotide sequence for the DNA template sequences can be determined based upon the sequencing reads. For example, for any particular partition, if two barcode beads are present, a sequence data set will be generated for each barcode bead. Through application of the method described here, once a basal threshold for the shared sequences between the two barcodes is achieved, the two sequence data sets can be merged to create a new nucleotide sequence. See example FIG. 3, which depicts an exemplary workflow.

In yet another embodiment, sequencing data can be excluded where more barcodes originate from a partition than is physically possible based on the average volume of the partitions and the volume of beads delivered to partitions. Data indicating such a high number of barcodes from a single partition is an indication that droplet integrity has been compromised and thus sequencing reads from any such barcodes can be excluded to improve sequencing resolution.

In another aspect, it has been discovered that contrary to common practice it can be beneficial for improving signal-to-noise in sequencing. The inventors surprisingly discovered that loading partitions at higher bead concentrations than a 1:1 average resulted in better signal to noise ratios.

Various metrics showed improvement when loading of partitions with multiple barcoded beads (beads with copies of barcode oligonucleotides attached). For example, in an ATAC-seq analysis, various criteria including Transcription Start Site (TSS) %, Fraction of reads in peaks (FRiP) % and TSS score were improved when increasing number of barcoded beads were introduced per droplet.

Thus, in some embodiments, methods comprise providing partitions in which at least 10%, 20%, 30%, 40%, 50%, 60% or 70% of the partitions have more than one barcoded particle (e.g., bead) per partition, linking the barcodes from the particles to sample DNA in the partitions, and then sequencing the barcoded sample DNA (for example in a bulk reaction as described above). Once the sequencing reads are generated, any method can be used to deconvolute the data to pool sequencing reads having different barcodes from the same partition. Thus, in some embodiments, one can use the methods described above involving determining the percent of identical fragments in common and combining sample reads to assume all such reads are from the same partition when the percent of identical fragments exceeds a threshold as discussed here. Other methods for deconvoluting the sequencing reads (determining whether reads come from the same or different partitions) can include, for example, those described in PCT WO2017/120531. For example, in some embodiments the method can involve providing in a partition a substrate comprising a barcode sequence or repeating clonal barcode sequences; and in the partition, associating a first particle conjugated to oligonucleotide primers comprising a first barcode sequence and a second particle conjugated to oligonucleotide primers comprising a second barcode sequence to a barcode sequence from the substrate; thereby generating a nucleic acid signature for the particles in the partition which can be used to distinguish barcodes in separate compared to the same partition (see PCT WO2017/120531). In other aspects for deconvoluting the sequencing reads (determining whether reads come from the same or different partitions), the method can comprise: forming partitions comprising forward primers comprising a barcode and a capture sequence complementary to the 3' sequence, or reverse complement thereof, of a target nucleic acid, wherein different partitions contain different forward primers comprising different barcode sequences, and a partition ID tag oligonucleotide comprising a reverse complement of the capture sequence and a variable partition ID tag sequence; in the partitions, hybridizing at least one forward primer to the partition ID tag oligonucleotide to form a hybridized product; performing amplification on the hybridized product to form amplicons, wherein at least some amplicons are formed from a forward primer and the partition ID tag oligonucleotide; and sequencing the amplicons, wherein if different forward primers form amplicons with the same variable partition ID tag sequence, the different forward primers are considered to be from the same partition. In some of those embodiments, the forward primer and partition ID tag oligonucleotide are linked to the same substrate when delivered to the partitions; or the partition ID tag oligonucleotide has a blocked 3' end such that a polymerase cannot extend the blocked 3' end during amplification; or the partition ID tag oligonucleotide comprises a double-stranded variable partition ID tag sequence and one or two single-stranded 3' ends comprising the reverse complement of the capture sequence. See, e.g., U.S. Provisional Patent Application No. 62/624,400.

Also provided are systems for receiving sequencing reads from barcoded DNA templates as described herein, determining in a pairwise manner frequency percent of sequencing reads of DNA template fragments shared between different barcodes; comparing the determined frequency percent of DNA template fragments shared between different barcodes to a threshold value, wherein if two barcodes have a determined frequency percent of DNA template fragments in common above the threshold value, the two barcodes are determined to be in the same partition; and generating a nucleotide sequence for the DNA template from the plurality of sequencing reads, wherein generating the nucleotide sequence comprises treating sequencing reads having different barcodes determined to be in the same partition as being from the same partition.

The above analysis can be performed in software on a computer or in a system as described herein. Any of the computer systems mentioned herein may utilize any suitable number of subsystems. Examples of such subsystems are shown in FIG. 1 in computer apparatus 10. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 1 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 977 (e.g., USB, FireWire). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of instructions from system memory 72 or the storage device(s) 79 (e.g., a fixed disk, such as a hard drive or optical disk), as well as the exchange of information between subsystems. The system memory 72 and/or the storage device(s) 79 may embody a computer readable medium. Any of the data mentioned herein can be output from one component to another component and can be output to the user.

A computer system can include a plurality of the same components or subsystems, e.g., connected together by external interface 81 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As used herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C # or scripting language such as Perl or Python using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the analytical (non-physical) steps of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

EXAMPLES

Example 1

Prophetic Example for Deconvolution of Bead Barcodes (See FIG. 3)

Human K562 cell line cells are harvested from culture, monitored for viability and washed by established methods to remove the culture media from the cell suspension. The cells are counted to a concentration of approximately 50 000 cells per μL and lysed to yield nuclei and tagmented according to the published OMNI protocol (Corces et al. Nature Methods 2017). Upon completion the tagmented nuclei are kept on ice. The tagmented nuclei are then encapsulated together with reagents that support PCR barcoding in droplets using barcoded gel beads. The gel bead concentration is chosen so that on average 2-4 beads are delivered per droplet. Thermal cycling is performed to barcode the target nucleic acid fragments. The products are Ampure bead purified to remove non-specific products and a second PCR is performed to increase the product concentration if required. A second purification occurs conditional on the 2nd PCR. The library is QCed for sequencing and sequenced. Bionformatic treatment of data occurs as described in FIG. 3 to identify barcode beads sharing partitions based on the methods described herein as well as generate ATAC specific metrics.

1. Align reads: Paired-end reads are aligned to the genome of their species using Burrows-Wheeler Aligner (BWA). See, e.g., Li H. and Durbin R. (2009) Fast and accurate short read alignment with Burrows-Wheeler Transform. *Bioinformatics*, 25:1754-60.
2. Filter low quality alignments: Alignments with a mapping quality (MAPQ)<30 are removed. All fragments remaining have a ≥90% probability of correct mapping.
3. Deduplicate identical fragments for each bead barcode: Fragments with identical start and stop positions and the same barcode are deduplicated so that only a single fragment with those traits is used downstream. The unique fragment count for each bead is recorded.
4. Count identical fragments pairwise between each bead barcode: For each pair of beads, the number of fragments with identical start and stop sites are counted.
5. Determine percentage fragment overlap between each bead barcode: The percentage of fragments overlapping between each barcode pair that has at least one identical fragment is calculated using the following formula:

$$\% \text{ Fragment Overlap} = \frac{N common}{(Nbarcode1 + Nbarcode2 - Ncommon)}$$

Nbarcode1=Number of fragments associated with barcode 1
Nbarcode2=Number of fragments associated with barcode 2
Ncommon=Number of identical fragments shared between barcode 1 and barcode 2

6. Find threshold point in smoothed distribution of bead-pair fragment overlap percentages: The distribution of fragment overlap percentages for each bead barcode pair is plotted and smoothed. The inflection point, where two high points surround a low point, in this distribution is used to divide valid from invalid bead merges.
7. Merge beads with fragment overlap percentage>threshold and assign cell barcode: All beads with a fragment overlap percentage greater than or equal to the inflection point threshold are merged. Merged beads are assigned a unique cell/droplet/partition level barcode.
8. Deduplicate within cell/droplet/partition barcode: For beads that were merged, a second round of deduplication of identical fragments is performed to generate a single fragment in place of the identical ones that were used to generate the merge. A filtered set of alignments containing cell/droplet/partition barcodes is output, for example as a .bam file.
9. Call peaks: The "peak calling" program MACS2 (Zhang Y, et al. (2008) Model-based Analysis of ChIP-Seq (MACS), *Genome Biology*, 2008; 9(9):R137) is used to call peaks on the .bam file generated at the completion of bead merging (step 8).
10. Calculate signal to noise metrics for pseudobulk (cell barcodes ignored) data:
    TSS %: The .bam file generated in step 8 is "intersected" with a .bed file of annotated transcription start sites for the genome to which the reads were aligned. The TSS % is the fraction of reads that overlap at least one base within 2 kb upstream or downstream of an annotated transcription start site.

$$TSS \% = \frac{Ntss}{(\text{Total alignments})} \times 100$$

FRIP: The .bam file generated in step 8 is "intersected" with a .bed file of peaks generated by MACS2. The fraction of reads in peaks is the percentage of reads that overlap at least one base with a peak.

$$FRIP = \frac{Nreads \cdot in \cdot peaks}{(\text{Total alignments})} \times 100$$

TSS Enrichment Score: Using only the reads that fall within a +/−2 kb window around the annotated transcription start site, a normalized score is calculated by:
a. Calculating the average read depth in the 100 bp regions flanking the +/−2 kb TSS window
b. Calculating the read depth at the transcription start site—the center of the +/−2 kb TSS window
c. Dividing (b) by (a)

$$TSS \text{ Enrichment} = \frac{\text{Read depth at center of } TSS \text{ window}}{\text{Averaged read depth at 100 base pairs flanking } TSS \text{ window}}$$

Example 2

Figure 12:
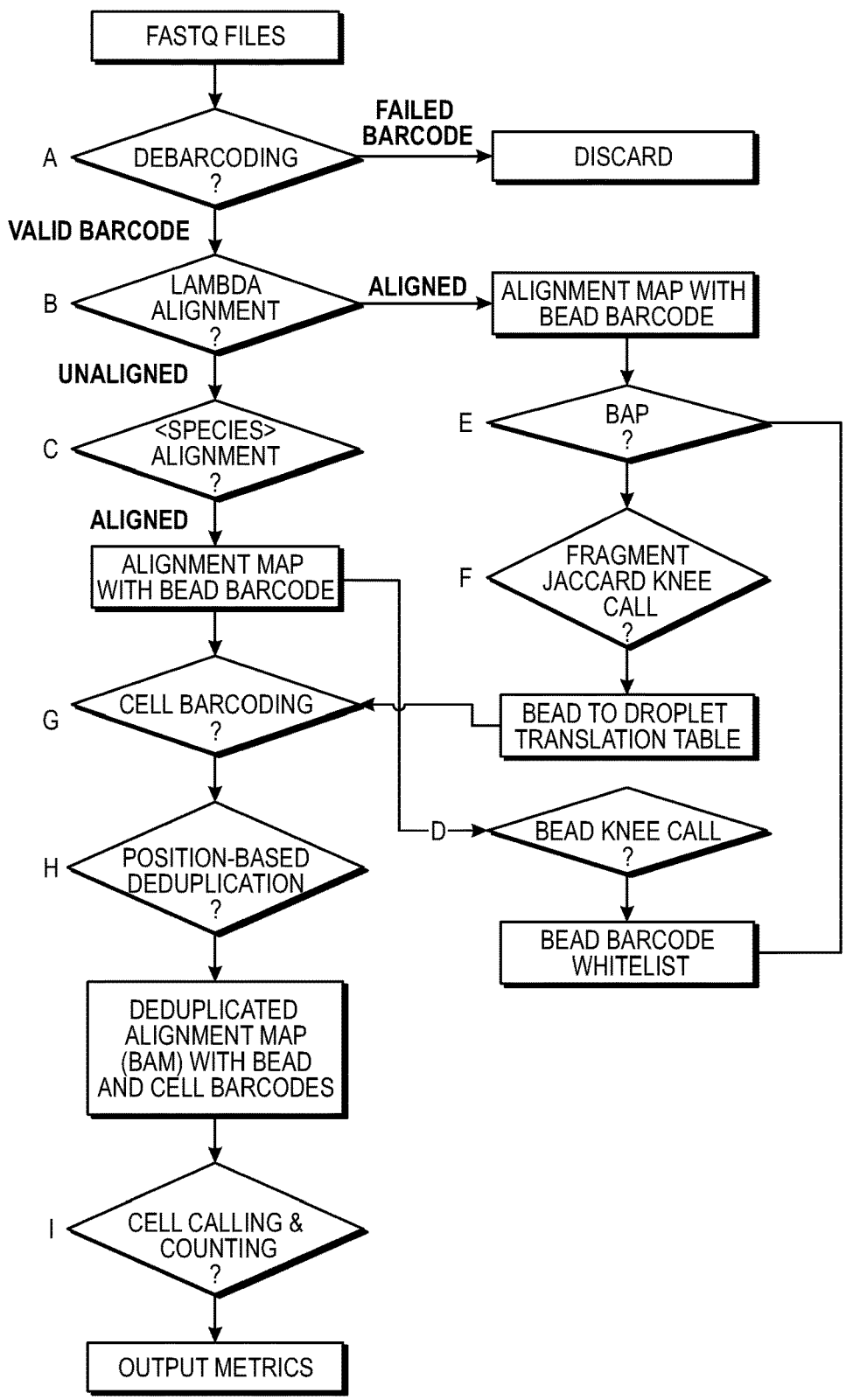
FIG. 12 illustrates identification of a threshold value on the left of the figure. After a jaccard index is calculated from alignments to the lambda genome (the source of exogenous DNA) and pairwise comparisons are performed across the barcode space, barcodes with jaccard indices above an algorithmically-defined threshold being merged to generate droplet level barcodes. The number of reads per droplet level barcode are plotted in descending order. Droplet level barcodes that have a higher number of reads over background, i.e., data points to the left of the knee, are inferred to represent cells. The right portion of the figure shows a bioinformatics flow path for assigning barcodes to partitions based on exogenous DNA in partitions.
Figure 12:
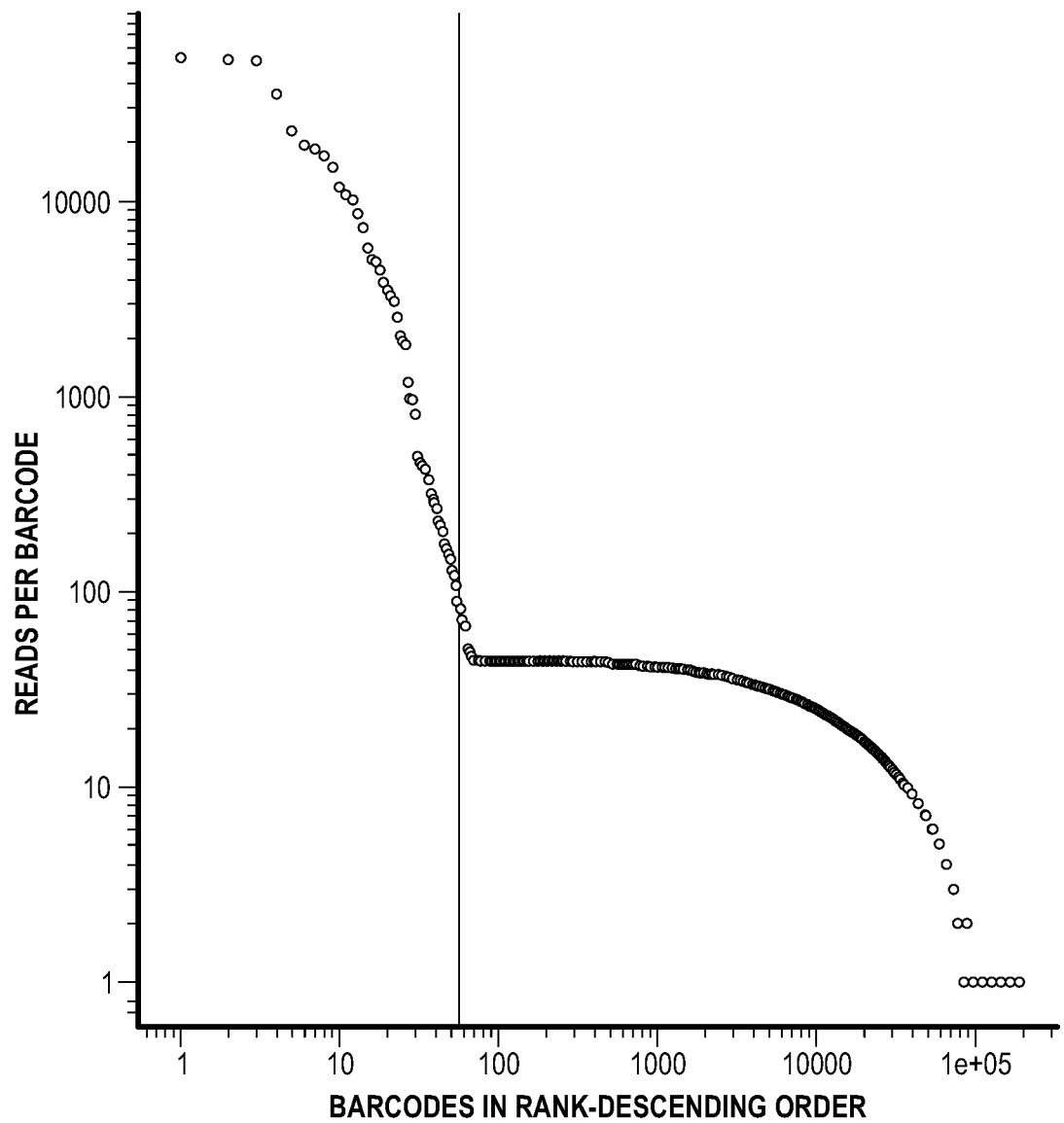

FIG. 12 depicts analysis of barcoding from exogenous fragmented DNA in droplets. Tagmented Lambda genome DNA was used as an example of exogenous fragmented DNA in single-cell deconvolution process. In brief, Lambda genome was randomly tagmented and labeled with a specific sequence that is complementary to the capture sequence of barcode-oligo by transposase. The tagmented Lambda fragments were added to the reaction during a single-cell partitioning step, whereby endogenous transcripts of single-cell and exogenous Lambda DNA fragments were captured by unique barcode-oligonucleotides in the same droplet through polymerase activity. After an in-droplet barcoding step, all droplets were disrupted and single-cell library of barcode-labeled DNA fragments were sequenced by next generation sequencing following the manufacturer's instructions. The result of sequencing was captured in FASTQ file format for subsequent sequence analysis using a bioinformatics pipeline described below and as depicted in FIG. 12.

The following explains various steps in the flow chart in FIG. 12.

A—Input FASTQ files (raw reads) are debarcoded using the Bio-Rad ATAC-Seq Toolkit. Reads with valid barcodes are passed forward to the next step in the workflow. Reads with invalid barcodes (no barcode, incorrect barcode structure, ambiguous barcode) are discarded from the analysis. Reads with valid barcodes have the barcode sequence moved from the DNA sequence of the read and into the read name.

B— Reads with valid barcodes are first aligned to the Lambda phage genome (found on the world wide web at neb.com/products/n3011-lambda-dna#Product %20Information) with the BWA-MEM algorithm. Reads aligned to the Lambda genome are passed to step X in the form of a BAM file with the bead barcode annotated to the alignment as the XB tag. Reads that do not align to the Lambda genome are passed to step C.

C— Reads unaligned to the Lambda genome, presumably those originating from cells in the experiment, are aligned to the genome of their species with the Spliced Transcripts Alignment to a Reference (STAR) aligner. Reads aligned in this step are passed to steps D and G in the form of a BAM file with the bead barcode annotated to the alignment as the XB tag. Reads that do not align in this step are discarded (not pictured).

D—A 'knee call' is performed on the beads using the Bio-Rad ATAC-Seq Toolkit. The number of unique genomic fragments for each bead barcode are counted then log 10 transformed. A gaussian kernel density estimate is generated for the transformed genomic fragments by bead barcode distribution. Finally, the inflection point most likely representing the distinction between beads exposed to cells vs. beads in empty droplets is determined. All beads below this threshold are excluded from further analysis. A 'whitelist' of barcodes is passed forward to step E.

E—Lambda alignments to beads on the whitelist generated in step D are processed through bead deconvolution. The count of the number of identical and unique alignments between each pair of beads is calculated. The fragment overlap index (=ratio of identical to unique fragments) for each pair of beads is calculated and passed forward to step F. A high fragment overlap index indicates a high number of identical fragments between two beads, a low probability occurrence when two beads are in different droplets.

F—A 'knee call' is performed on this distribution using the same methodology outlined in step D with the inflection point being the Jaccard index at which two beads are 'seeing' fragments from the same cell vs. chance level observation of identical fragments on beads in separate droplets. All bead barcodes with Jaccard indices above this threshold value are merged. This generates a new suite "droplet" barcodes. The primary output of this step is passed to step G as a bead barcode to droplet barcode translation table with many beads to one droplet barcode relationships are captured.

G—The bead to droplet translation table from step F and the BAM file from step C are combined to annotate the droplet barcode onto all alignments from beads that were determined to be in the same droplet based on calculations in steps E and F. This 'cell barcoded' BAM file is passed forward into step H.

H—Reads aligned to the exact same position with the same cell (used interchangeably with "droplet") barcode are deduplicated, retaining only one alignment among the >1 beads in a droplet with an alignment to a given genome position. This deduplicated BAM file is passed forward to step I for cell calling and counting.

I—A knee call is performed based on the number of unique genic reads per cell barcode using identical methodology as in steps D and F.

Example 3

Figure 13:
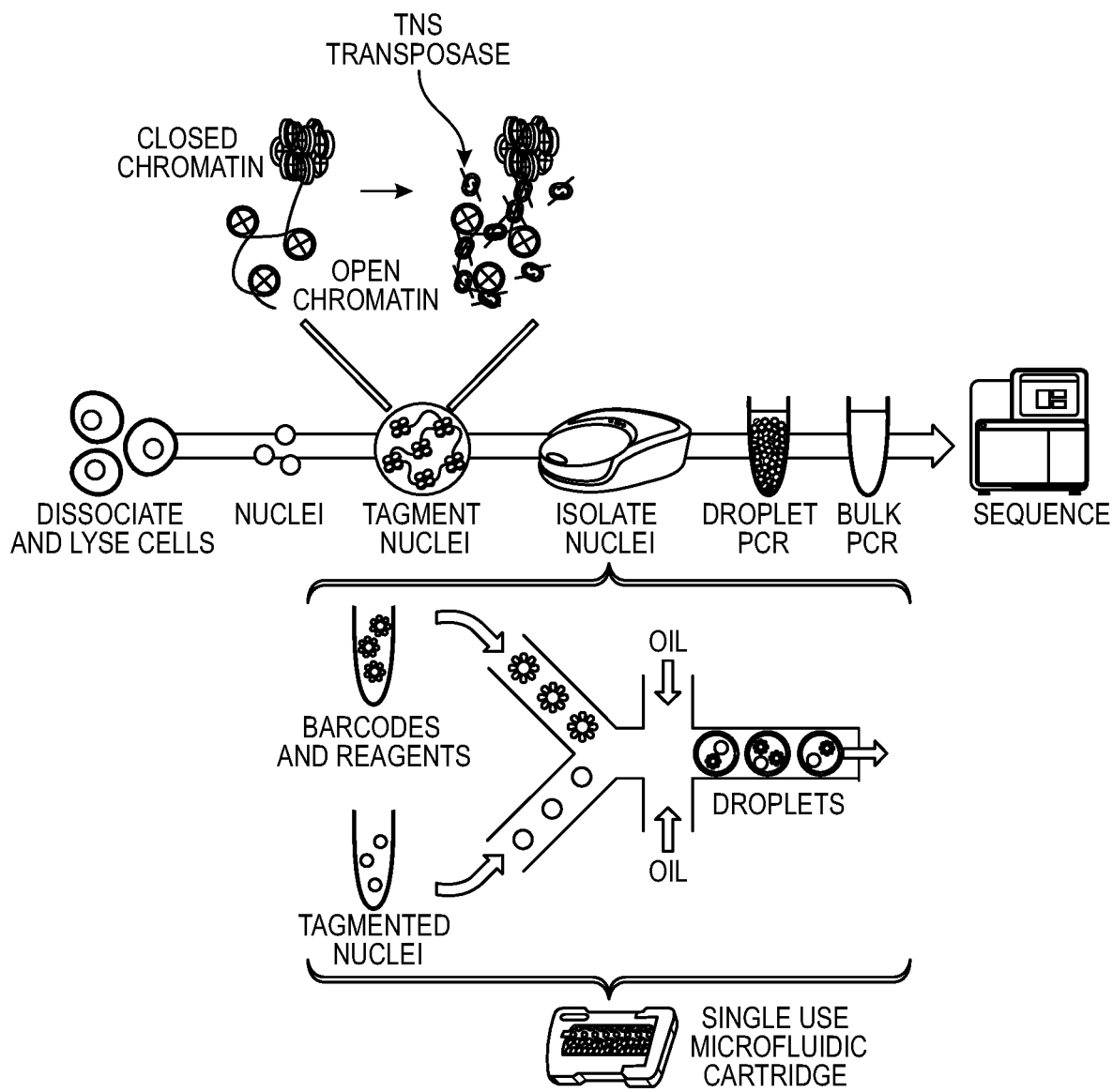
FIG. 13: depicts a mixed species single cell ATAC-Seq experiment.
Figure 14:
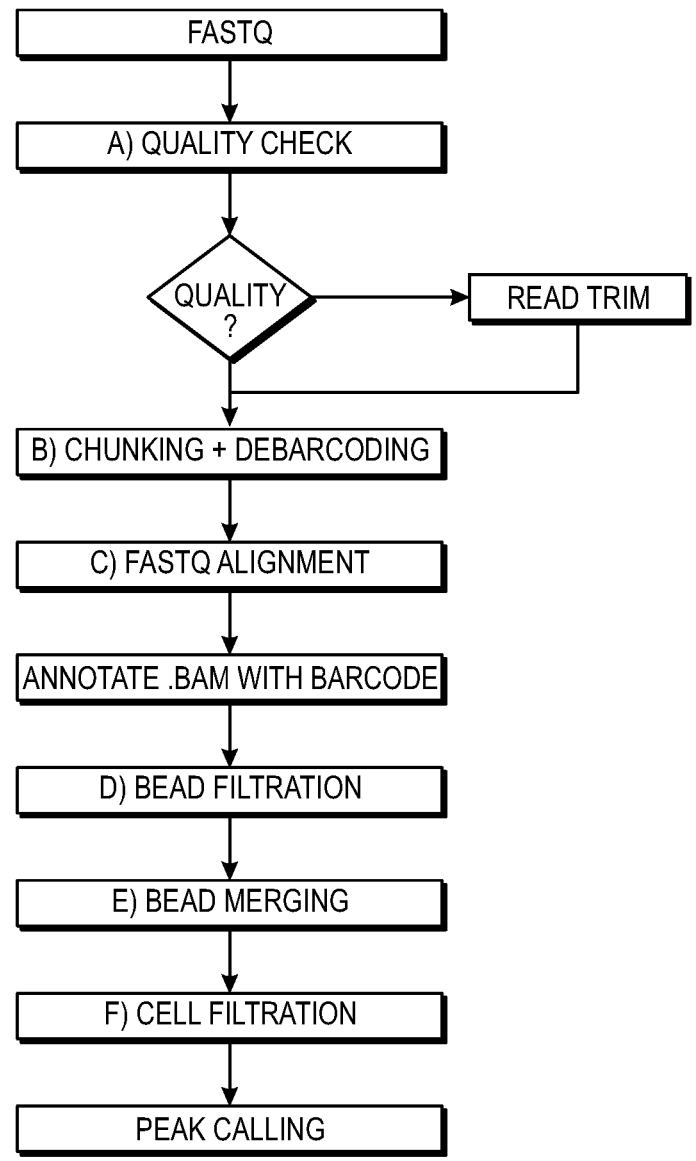
FIG. 14 depicts a bioinformatic pipeline for bead co-localization to single droplets using single cell ATAC-Seq data.
Figure 15:
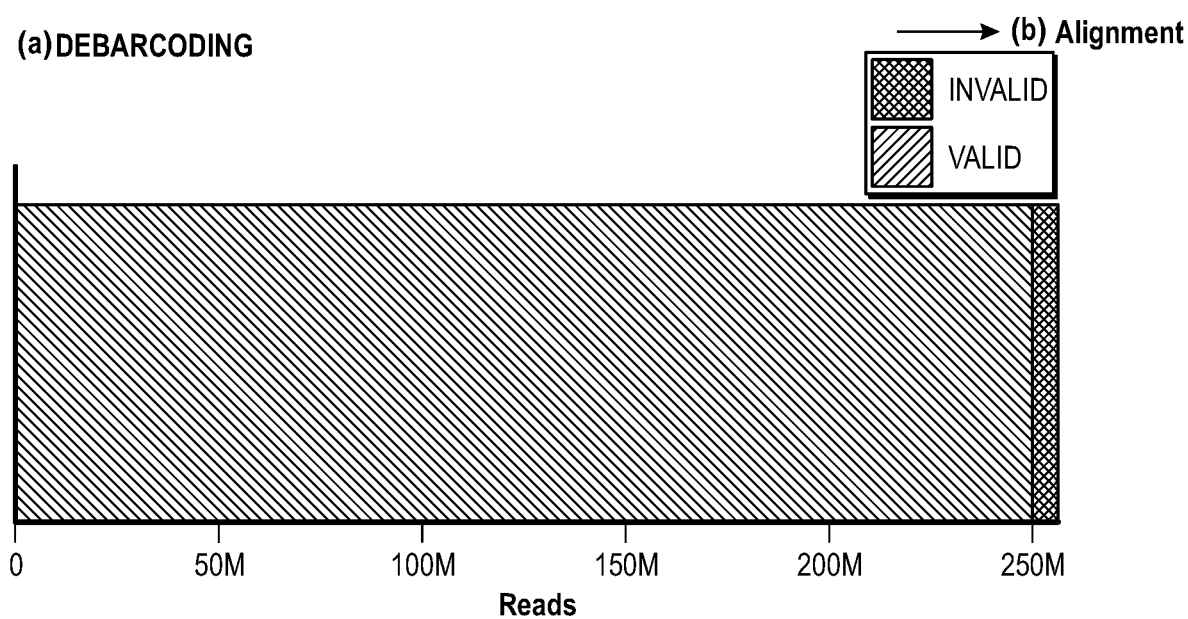
FIG. 15. depicts an example of merging of bead data from the same partition during an ATAC-Seq experiment.
Figure 15:
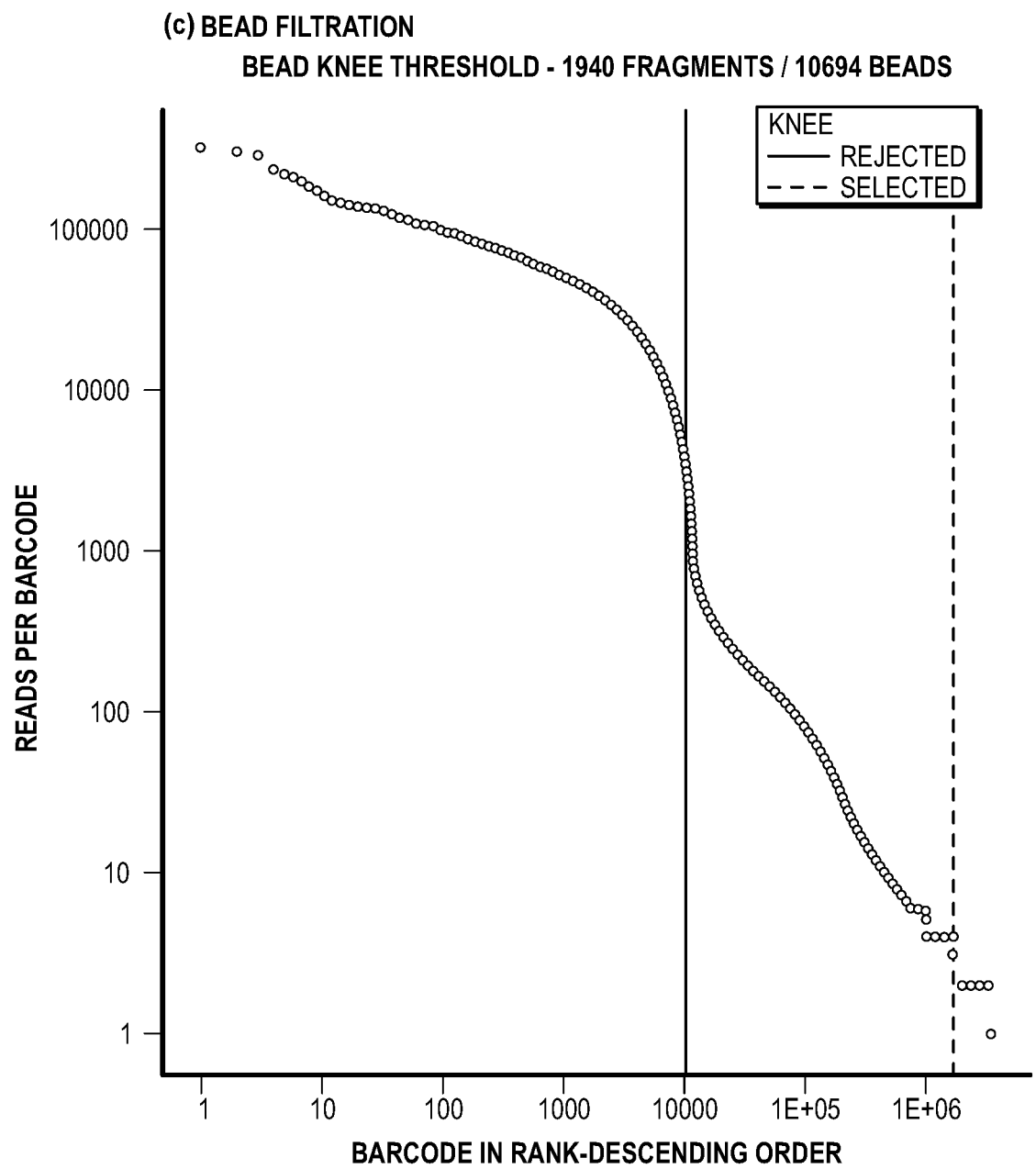
Figure 15:
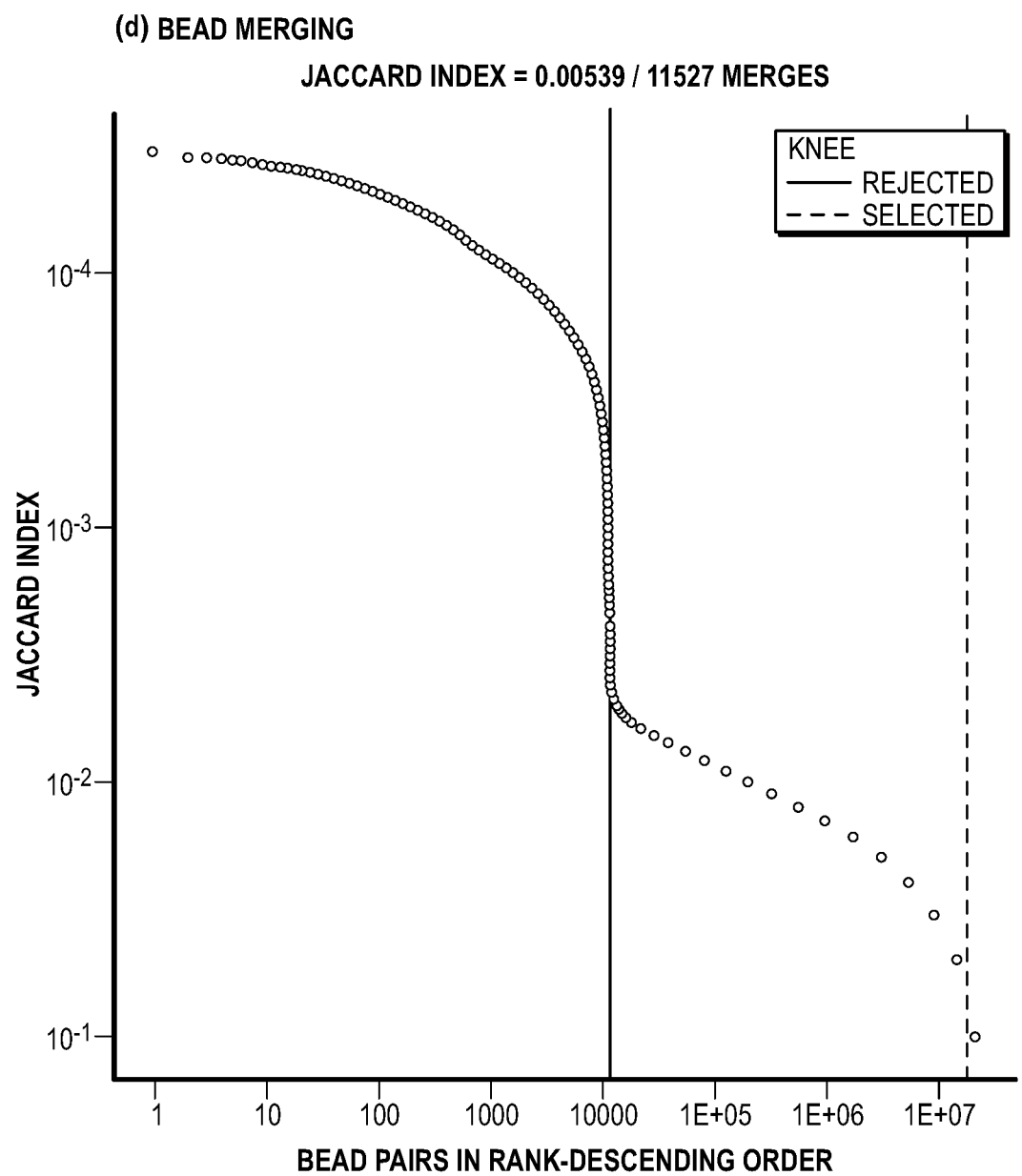
Figure 15:
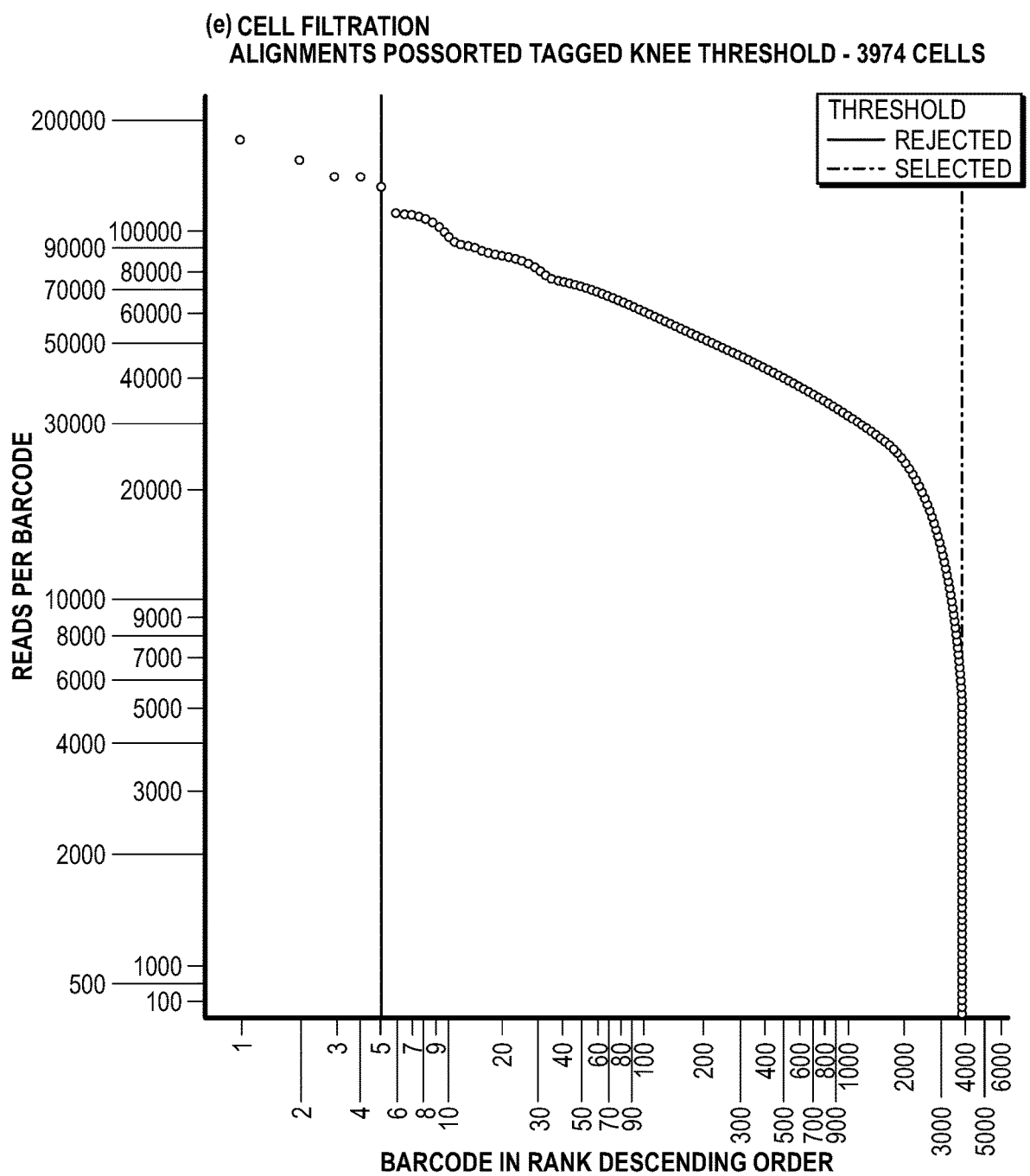
Figure 15:
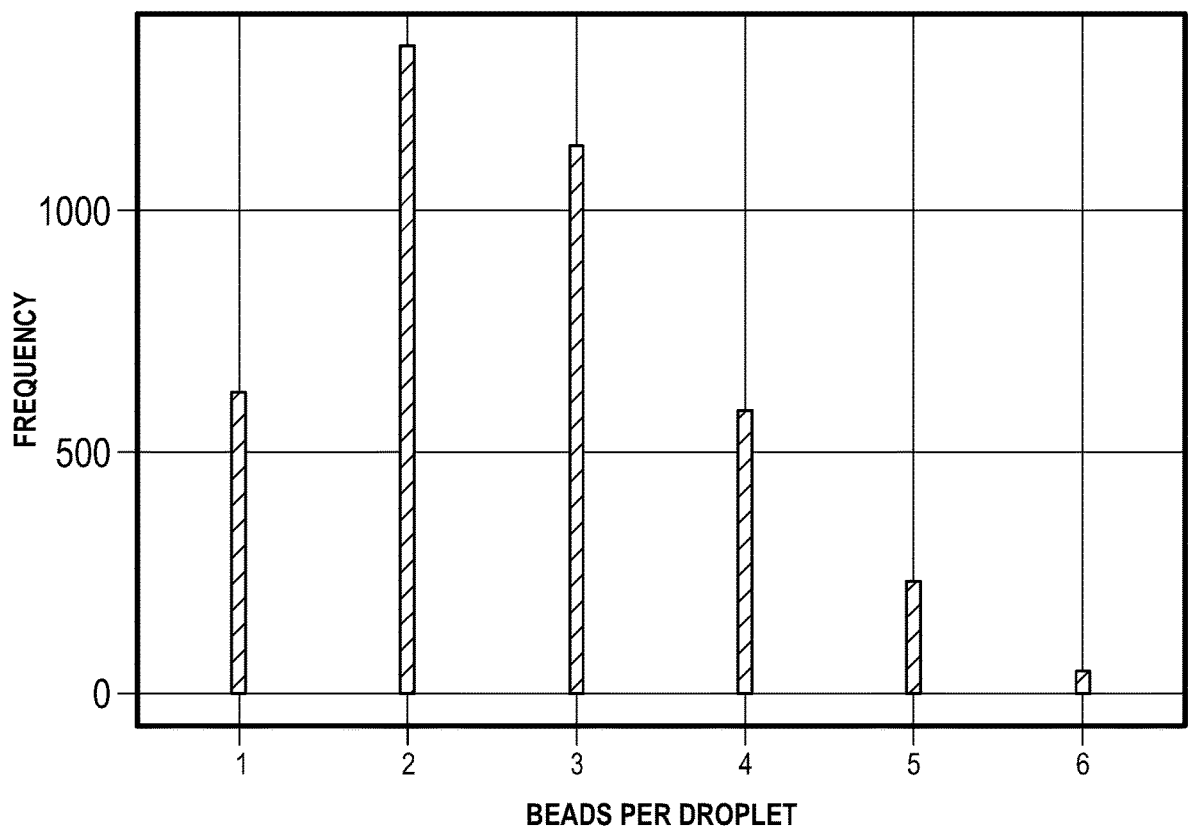

FIGS. 13-15 depict an exemplary work flow. FIG. 13 shows a mixed species single cell ATAC-Seq experiment. An equal number of mouse and human cell lines are combined and then subjected to the workflow illustrated below. Nuclei are prepared from lysed cells and tagmented with Tn5 transposase in bulk (tubes). The tagmented nuclei together with barcodes and PCR reagents are flowed into a microfluidic cartridge and combined at the point where droplets are made. The droplets are collected into a tube and subjected to a first round of PCR. The droplets are then broken and subjected to a second round of PCR. The adaptered DNA fragments are then sequenced.

FIG. 14 depicts a bioinformatic pipeline for bead co-localization to single droplets using single cell ATAC-Seq data. A) Quality check. Per-base sequence quality, adapter contamination, and abundant sequences are calculated and a decision is made whether bases should be trimmed from FASTQ reads. B) Chunking and debarcoding. Barcode sequences are extracted and filtered in preparation for alignment. C) FASTQ alignment. Reads are aligned to a genome with the STAR aligner. Reads aligned are passed to the next step in the form of a BAM file that has barcodes annotated in the XB tag. D) Bead filtration. The number of unique genomic fragments for each bead barcode are counted then log 10 transformed. A gaussian kernel density estimate is generated for the transformed genomic fragments by bead barcode distribution. Finally, the inflection point most likely representing the distinction between beads exposed to cells vs. beads in empty droplets is called. All beads below this threshold are excluded from further analysis. A 'whitelist' of barcodes is passed forward. E) Bead merging. A 'knee call' is performed on this distribution using the same methodology outlined in step D with the inflection point being the Jaccard index at which two beads are 'seeing' fragments from the same cell vs. chance level observation of identical fragments on beads in separate droplets. All bead barcodes with Jaccard indices above this threshold value are merged. This generates a new suite "droplet" barcodes that represent cells. The primary output of this step is passed to step F as a bead barcode to droplet/cell barcode translation table with many beads to one droplet barcode relationships are captured. F) Cell filtration. A knee call is performed based on the number of unique genic reads per cell barcode using identical methodology as in steps D and E. Peaks are then called by finding genome regions that are enriched with aligned reads.

FIG. 15 depicts an example of bead merging during an ATAC-Seq experiment. After running the experiment described in FIG. 13 with approximately 5000 cells input combining both mouse and human cells and running the bioinformatic pipeline in FIG. 14 the following ATAC-Seq data can be generated, including bead merging post co-localization to single droplets. After (a) debarcoding and (b) alignment, beads with high signal are identified as data points to the left of the knee, delineated by the vertical solid line, as shown in the bead filtration knee plot (c). % shared fragments between barcodes are calculated and beads are merged as points to the left of the vertical blue line in the bead merging knee plot (d). Cell data points are identified by a high unique genomic fragment to the left of the vertical line in (e). In this experiment 3974 cells were identified with greater than 25 thousand average unique fragments per cell. A histogram of calculated beads per droplet is shown in (f). From FIG. 15:

| Metric | Value |
|---|---|
| A) | |
| Input reads | 256,080,695 |
| Reads with Valid Barcode | 251,028,469 |
| % Reads with Valid Barcode | 98 |

| Metric | Value |
| --- | --- |
| B) | |
| Total Input Read Pairs | 251,028,469 |
| Total PF Read Pairs | 242,075,922 |
| Read 1 PF | 242,075,922 |
| Read 2 PF | 242,075,922 |
| PF Read 1 Aligned | 239,699,342 |
| % PF Read 1 Aligned | 99 |
| % Input Read 1 Aligned | 96.4 |
| PF Read 2 Aligned | 240,279,664 |
| % PF Read 2 Aligned | 99.3 |
| % Input Read 2 Aligned | 96.4 |
| Countable Fragments | 223,343,253 |
| % Input Pairs as Countable Fragments | 89 |
| Duplicate Fragments | 71,553,650 |
| % Duplicate Fragements | 32 |
| Unique Mitochondrial Fragments | 9,717,474 |
| % Mitochondrial Fragments | 6.4 |
| Unique Nuclear Fragments | 140,729,333 |
| % Unique Nuclear Fragments | 92.7 |
| Blacklisted Fragments | 1,342,796 |
| % Blacklisted Fragemnts | 0.885 |
| 5th Percentile Insert Size | 48 |
| Mean Insert Size | 170 |

| Metric | Value |
| --- | --- |
| 95th Percentile Insert Size | 408 |
| Total Barcodes Observed | 3,776,461 |
| C) | |
| Beads Above Threshold | 10,694 |
| Bead Fragment Threshold | 1,942 |
| D) | |
| Total Cells | 3,974 |
| Average Unique Fragments per Cell | 25,179 |
| Mouse Cells | 1,951 |
| Human Cells | 1,919 |
| Crosstalk % | 2.62% |
| Cell Purity | 98.90% |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of generating a nucleotide sequence of a DNA template, the method comprising:
   (a) partitioning a nucleic acid sample into a plurality of partitions, the partitions comprising a particle comprising a solid support surface, the solid support surface having a plurality of oligonucleotide primers conjugated thereon, wherein the oligonucleotide primers comprise a barcode sequence and wherein different particles are distinguished by having different barcodes from one another, wherein at least some partitions have more than one particles per partition, and wherein different particles are conjugated to primers having different barcode sequences, wherein the nucleic acid sample is provided into the partitions as DNA template fragments or the nucleic acid sample is fragmented in the partitions to generate the DNA template fragments;

(b) in the partitions, linking oligonucleotide primers from the solid support to at least one DNA template fragment, thereby forming barcoded DNA template fragments;

(c) combining barcoded DNA template fragments from multiple partitions;

(d) generating a plurality of sequencing reads of the barcoded DNA templates;

(e) determining in a pairwise manner percent of sequencing reads of identical DNA template fragments shared between different barcodes;

(f) comparing the determined percent of identical DNA template fragments shared between different barcodes to a threshold value, wherein if two barcodes have a determined percent of identical DNA template fragments in common above the threshold value, the two barcodes are determined to be in the same partition; and (g) generating a nucleotide sequence for the DNA template from the plurality of sequencing reads, wherein generating the nucleotide sequence comprises treating sequencing reads having different barcodes determined to be in the same partition as being from the same partition;

thereby generating a nucleotide sequence of a DNA template.

2. A method of distinguishing differently barcoded sequence reads originating from different partitions from sequence reads having different barcodes but originating from the same partition, the method comprising:

(a) partitioning a nucleic acid sample into a plurality of partitions, the partitions comprising a particle comprising a plurality of oligonucleotide primers, wherein the oligonucleotide primers comprise a barcode sequence and wherein different particles are distinguished by having different barcodes from one another, wherein at least some partitions have more than one particles per partition, and wherein different particles are conjugated to primers having different barcode sequences, wherein the nucleic acid sample is provided into the partitions as DNA template fragments or the nucleic acid sample is fragmented in the partitions to generate the DNA template fragments;

(b) in the partitions, linking oligonucleotide primers from the particle to DNA template fragments, thereby forming barcoded DNA fragments;

(c) combining barcoded DNA fragments from multiple partitions;

(d) generating a plurality of sequencing reads of the barcoded DNA;

(e) determining in a pairwise manner percent of sequencing reads of identical DNA fragments shared between different barcodes; and (f) comparing the determined percent of identical DNA fragments shared between different barcodes to a threshold value, wherein if two barcodes have a determined percent of identical DNA template fragments in common above the threshold value, the two barcodes are determined to be in the same partition.

3. The method of claim 2, wherein at least a majority of the plurality of oligonucleotide primers associated with a particle comprise the same barcode sequence.

4. The method of claim 2, wherein the DNA fragments are sample DNA.

5. The method of claim 4, wherein methyl cytosines in the sample DNA has been converted for methylation analysis prior to the partitioning.

6. The method of claim 4, wherein the partitions comprise sample cells and the sample DNA is from the sample cells.

7. The method of claim 4, wherein the partitions comprise sample cells and the sample DNA is cDNA generated from the sample cells.

8. The method of claim 4, further comprising pre-encapsulating the sample cells in partitions.

9. The method of claim 2, wherein the partitions further contain sample DNA to be sequenced and the DNA fragments are exogenous to the sample DNA.

10. The method of claim 4, further comprising generating a nucleotide sequence for the sample DNA, wherein generating the nucleotide sequence comprises treating sequencing reads having different barcodes determined to be in the same partition as being from the same partition, thereby generating a nucleotide sequence of a DNA template.

11. The method of claim 2, wherein the DNA fragments comprise heterologous end adaptor sequences.

12. The method of claim 2, wherein the providing comprises randomly cleaving DNA.

13. The method of claim 12, wherein the randomly cleaving comprises contacting the DNA with a transposase that introduces heterologous end adaptor sequences into the DNA to form DNA fragments comprising the heterologous end adaptor sequences.

14. The method of claim 2, wherein at least 10% of the partitions have more than one particle per partition.

15. The method of claim 2, wherein generating the nucleotide sequence comprises excluding sequencing reads from partitions comprising more particles than would be predicted by a Poisson distribution.

16. The method of claim 2, comprising excluding sequencing reads from partitions comprising more particles than are physically possible as determined by the size of the particle in comparison to the size of the partition.

17. The method of claim 2, wherein the particle is composed of a hydrogel that contains the oligonucleotides.

18. The method of claim 2, wherein the particle comprises a solid surface to which the oligonucleotides are conjugated.

19. The method of claim 17, wherein the oligonucleotides are released from the particles in the partitions.

* * * * *